United States Patent [19]

Himmelsbach et al.

[11] Patent Number: 5,260,278

[45] Date of Patent: Nov. 9, 1993

[54] DIOL-CONTAINING RENIN INHIBITORS

[75] Inventors: Richard Himmelsbach, San Jose, Calif.; John C. Hodges, Ann Arbor, Mich.; James S. Kaltenbronn, Ann Arbor, Mich.; William C. Patt, Chelsea, Mich.; Joseph T. Repine, Ann Arbor, Mich.; Ila Sircar, Ann Arbor, Mich.

[73] Assignee: Warner-Lambert Company, Morris Plains, N.J.

[21] Appl. No.: 678,469

[22] Filed: Apr. 1, 1991

Related U.S. Application Data

[60] Division of Ser. No. 321,638, Mar. 15, 1989, Pat. No. 5,036,053, which is a continuation-in-part of Ser. No. 199,990, May 27, 1988, abandoned.

[51] Int. Cl.$^5$ .................. A61K 37/02; C07D 265/30; C07D 295/26; C07K 5/06
[52] U.S. Cl. .................. 514/19; 514/237.8; 514/399; 530/860; 544/159; 548/342.1; 548/342.5
[58] Field of Search .................. 514/17, 18, 19, 237.8, 514/399; 530/330, 331, 332, 860; 544/159; 564/153; 548/342, 342.1, 342.5

[56] References Cited

U.S. PATENT DOCUMENTS

| 5,036,054 | 7/1991 | Kaltenbronn et al. | 514/18 |
| 5,122,514 | 6/1992 | Boger et al. | 514/252 |
| 5,122,523 | 6/1992 | Morishima et al. | 514/237.8 |
| 5,178,877 | 1/1993 | Garren et al. | 514/19 |

FOREIGN PATENT DOCUMENTS 018485  6/1986  European Pat. Off.

OTHER PUBLICATIONS

Denkewalter et al., "Progress in Drug Research", vol. 10 pp. 510–512 (1966).
Burger, "Medicinal Chemistry", second edition, pp. 565–571, 578–581, 600–601 (1960).
Plattner et al., "Renin Inhibitors Dipeptide Analogues" J. Med. Chem. 1988, 31, 2277–2288.
Bolis et al., "Renin Inhibitors. Dipeptide Analogues" J. Med. Chem. 1987, 30, 1729–1737.
Haber et al., "Renin Inhibitors: A Search . . . " Journal of Card. Pharm. 10(Suppl. 7):554–558 (1987).

*Primary Examiner*—Jeffrey E. Russel
*Attorney, Agent, or Firm*—Elizabeth M. Anderson

[57] ABSTRACT

The invention concerns novel renin-inhibitory peptides which are useful for treating renin-associated hypertension, congestive heart failure, hyperaldosteronism, and diseases caused by retroviruses including HTLV-I and -III. Processes for preparing the peptides, compositions containing them, and methods of using them are included. Also included is a diagnostic method which uses the compounds to determine the presence of renin-associated hypertension, or hyperaldosteronism.

7 Claims, No Drawings

DIOL-CONTAINING RENIN INHIBITORS

CROSS REFERENCE TO RELATED APPLICATION

This is a divisional application U.S. Ser. No. 07/321,638 filed Mar. 15, 1989, now U.S. Pat. No. 5,036,053 issued Jul. 30, 1991, which is a continuation-in-part of U.S. application Ser. No. 199,990 filed May 27, 1988, now abandoned.

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renins have been sought as agents for control of hypertension, congestive heart failure, and hyperaldosteronism.

European Application No. 86/106458 covers certain renin-inhibiting N-(acyldipeptidyl)-aminoglycols of the formula

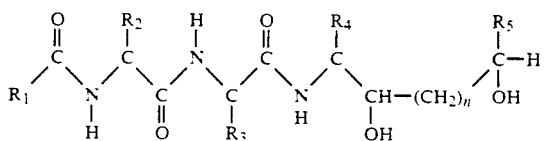

wherein $R_1$ is alkoxy containing one to six carbon atoms or lower alkyl containing one to six carbon atoms; $R_2$ is benzyl or napthylmethyl, $R_2$ is lower alkyl containing one to six carbon atoms or imidazolemethyl; $R_4$ is benzyl, $R_5$ is hydrogen or lower alkyl and n is 0. These compounds are useful as renin inhibitors.

European Application No. 87/100424 covers renin inhibiting peptidyl-amino-diols of formula

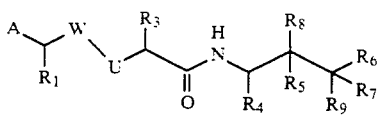

wherein A is a substitutent; W is C=O or CHOH; U is $CH_2$ or $NR_2$; $R_1$ is lower alkyl, cycloalkylmethyl, benzyl, -methoxybenzyl, halobenzyl, (1-naphthyl)methyl, (2-naphthyl)methyl, (4-imidazoyl)methyl, α,α-dimethylbenzyl, 1-benzyloxyethyl, phenethyl, phenoxy, thiophenoxy or anilino; $R_3$ is lower alkyl, (alkoxy)alkoxy]alkyl, (thioalkoxy)alkyl, lower alkenyl, benzyl or heterocyclic ring substituted methyl; $R_4$ is lower alkyl. cycloalkylmethy or benzyl; $R_5$ is vinyl, formyl, hydroxymethyl or hydrogen; $R_7$ is hydrogen or lower alkyl; $R_8$ and $R_9$ are independently selected from OH and $NH_2$; and $R_6$ is hydrogen, lower alkyl, vinyl or arylalkyl.

Structurally the positions of the various amino acids of the compounds of the instant invention may be designated by reference to the octapeptide which is the minimal angiotensinogen sequence cleaved by renin, namely:

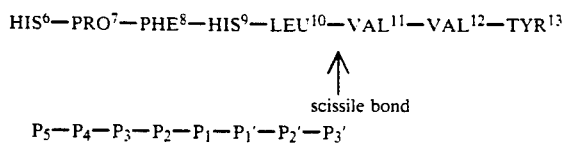

A designation for the compounds of this invention is illustrated below. The CAD is considered to occupy the $P_1$-$P_1'$ positions. For example

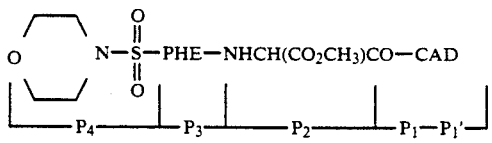

The present invention concerns novel peptides which inhibit renin. It also concerns pharmaceutical compositions containing these novel peptides, methods of treating renin-associated hypertension, congestive heart failure, and hyperaldosteronism, as well as the use of the peptides as diagnostic tools, and the methods for preparing the peptides.

Since HIV protease, like renin, is an aspartyl protease, these compounds can also be used to treat diseases caused by retroviruses including HTLV-I and -III.

SUMMARY OF THE INVENTION

The present invention relates to novel peptides of the formula $$A-X-Y-W \quad (I)$$

and the pharmaceutically acceptable acid addition salts thereof wherein A, X, Y, W are as defined herein below.

The invention also includes pharmaceutical compositions comprising an effective amount of the above peptide of formula I in admixture with a pharmaceutically acceptable carrier or excipient and a method for treating renin-associated hypertension in a patient suffering therefrom comprising administering to said patient the above pharmaceutical composition in unit dosage form.

Further the invention includes a pharmaceutical composition comprising an effective amount of a peptide of formula I above in admixture with a pharmaceutically acceptable carrier or excipient, and a method for treating hyperaldosteronism in a patient suffering therefrom comprising administering to said patient the above pharmaceutical composition in unit dosage form.

Further the invention includes a pharmaceutical composition comprising an effective amount of a peptide of formula I in admixture with a pharmaceutically acceptable carrier or excipient, and a method for treating congestive heart failure in a patient suffering therefrom comprising administering to said patient the above pharmaceutical composition in unit dosage form.

The present invention also includes the use of peptides of formula I above as diagnostic tools for the identification of cases of hypertension due to renin excess.

The present invention also includes the use of peptides of formula I to treat diseases caused by retroviruses.

The invention further includes methods for preparing peptides of formula I above.

DETAILED DESCRIPTION

The following table provides a dictionary of the terms used in the description of the invention.

TABLE I

| Abbreviated Designation | |
|---|---|
| | Amino Acid |
| PHE | L-Phenylalanine |
| HOMOPHE | Homophenylalanine |
| LYS | L-Lysine |
| NAPHTHYLALA | 1-Naphthylalanine |
| CYCLOHEXYLALA | Cyclohexylalanine |
| TYR(OMe) | O-Methyl-L-tyrosine |
| TYR | L-Tyrosine |
| TZA | 4-Thiazolylalanine |
| HIS | L-Histidine |
| ASN | L-Asparagine |
| | C-Terminal Group |
| CAD | —HNCHCH(OH)CH(OH)CH$_2$CH(CH$_3$)$_2$<br>$\quad\;\;$\|<br>$\quad\;\;$CH$_2$<br>$\quad\;\;$\|<br>$\quad\;\;$(cyclohexyl) |
| CAH | —NHCHCH(OH)CH(OH)CH$_2$CH(CH$_3$)$_2$<br>$\quad\;\;$\|<br>$\quad\;\;$CH$_2$<br>$\quad\;\;$\|<br>$\quad\;\;$(cyclohexyl) |
| | Protecting Group |
| Z | Benzyloxycarbonyl |
| BOC | Tert-butyloxycarbonyl |
| TRT | Triphenylmethyl |
| | Acyls |
| IVA | Isovaleryl |
| BNMA | Bis-(1-naphthylmethyl)acetyl |
| BBSP | 2-Benzyl-3-(t-butylsulfonyl) propionyl |
| Z-BMA | 3-(Benzyloxycarbonylamino)-3-methylbutanoyl |
| BMA | 3-Amino-3-methylbutanoyl |
| | Esters With |
| —OCH$_3$ | Methanol |
| —OC$_2$H$_5$ | Ethanol |
| —OCH(CH$_3$)$_2$ | 2-Propanol |
| —OC(CH$_3$)$_3$ | tert-Butanol |
| | Solvents and Reagents |
| CHCl$_3$ | Chloroform |
| DMF | N,N-Dimethylformamide |
| DMSO | Dimethylsulfoxide |
| HOBT | Hydroxybenzotriazole |
| DCC | N,N'-Dicyclohexylcarbodiimide |
| HOAc | Acetic acid |
| Et$_3$N | Triethylamine |
| THF | Tetrahydrofuran |
| CH$_2$Cl$_2$ | Dichloromethane |
| MeOH | Methanol |
| EtOAc | Ethyl acetate |

The peptides of the present invention are represented by the formula $$A—X—Y—W \qquad (I)$$

or a pharmaceutically acceptable acid addition salt thereof, wherein

A is BOC, IVA, NVA, BNMA, BMA, BBSP, Z

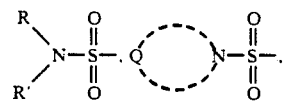

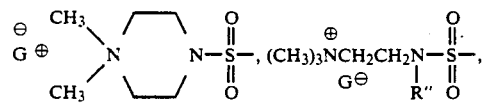

wherein G is hydroxyl or halide,

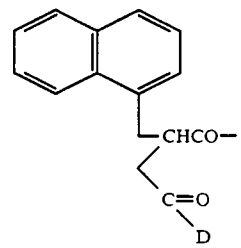

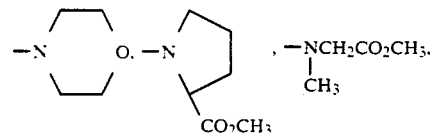

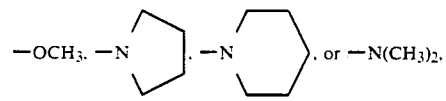

wherein R and R' are each independently hydrogen, straight or branched chain lower alkyl, or R and R' are P—CH$_2$CH$_2$, wherein P can be OR", SR", NR"R''' or NR"COR" wherein R" and R''' can be hydrogen, or straight or branched chain lower alkyl, or P is NR"R''' wherein forms a heterocyclic ring containing from 4 to 6 carbon atoms or containing one or more atoms selected from S, O, or NR".

is a saturated ring containing 1 to 5 carbon atoms wherein Q is CH$_2$, O, S, or NR;

X is absent, PHE, HOMOPHE, NAPHTHYLALA, CYCLOHEXYLALA, TYR, or TRY(OMe) with the proviso that when A is BNMA, BBSP, or

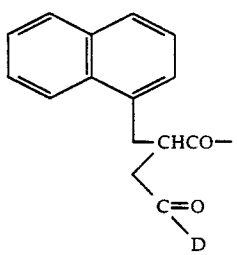

X is absent;
Y is GLY,

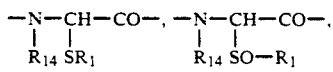

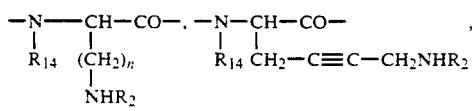

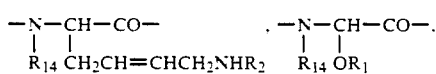

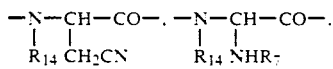

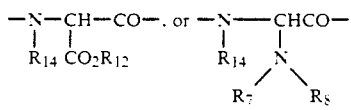

wherein $R_1$ is lower alkyl, alkenyl, alkynyl, aryl, heteroaryl, aralkyl, $(CH_2)_n$-$NHR_2$, wherein n is an integer of from 2 to 4, and $R_2$ is

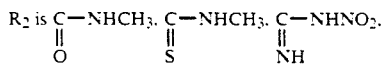

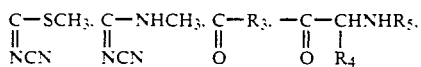

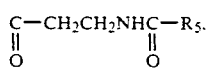

wherein $R_3$ is hydrogen, lower alkyl, or aryl, $R_4$ is H, lower alkyl or aralkyl, $R_5$ is

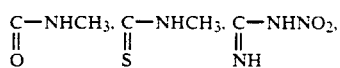

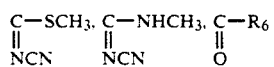

wherein $R_6$ is hydrogen, lower alkyl or aryl, wherein $R_7$ is

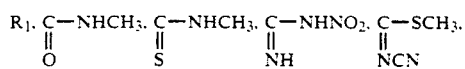

-continued

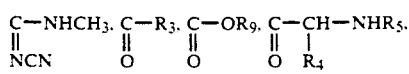

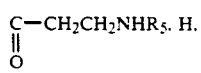

wherein $R_{12}$ is hydrogen, lower alkyl, alkenyl, alkynyl, aralkyl, or

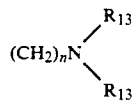

wherein $R_8$ is lower alkyl or together with $R_7$, when $R_7$ is lower alkyl, forms of heterocyclic ring containing from 4 to 6 carbon atoms optionally containing one or more S, O, or NR; $R_9$ is alkyl, or aralkyl; $R_{13}$ is H or lower alkyl; $R_{14}$ is H or $CH_3$, and Y is also HIS or TZA with the proviso that when Y is HIS or TZA, A is BBSP;
W is

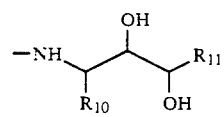

where $R_{10}$ is lower alkyl, cycloalkyl, cycloalkylmethyl or benzyl and $R_{11}$ is lower alkyl.

Preferred compounds of the present invention are those of formula I wherein A is BOC, BNMA, BBSP, BMA,

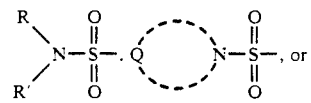

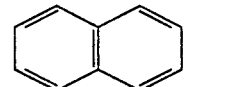

wherein D is

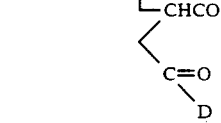

X is absent, PHE, NAPHTHYLALA, TYP(OMe) with the proviso that when A is BNMA, BBSP, or X is absent;

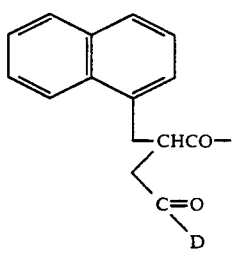

Y is

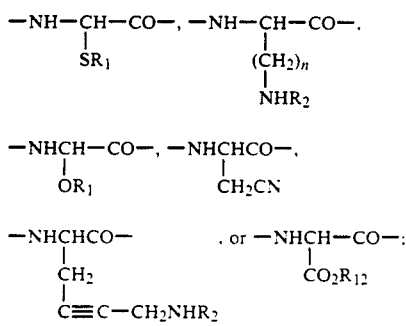

and W is

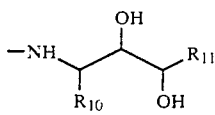

where $R_{10}$ is cycloalkyl or cycloalkylmethyl.

more preferred compounds of the present invention are those of formula I wherein Y is

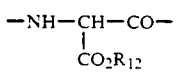

wherein $R_{12}$ is hydrogen, or lower alkyl.

Other more preferred compounds of the present invention are those of formula I wherein Y is

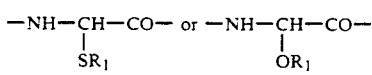

wherein $R_1$ is lower alkyl, alkenyl, or alkynyl.

Other more preferred compounds of the present invention are those of formula I wherein Y is

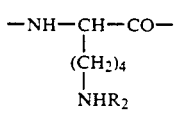

wherein $R_2$ is

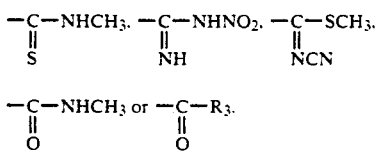

Other more preferred compounds of the present invention are those of formula I wherein Y is

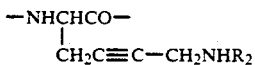

wherein $R_2$ is

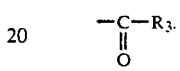

Other more preferred compounds of the present invention are those of formula I wherein Y is

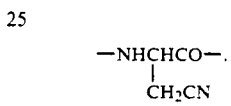

Still other preferred compounds of the present invention are those of formula I wherein A is

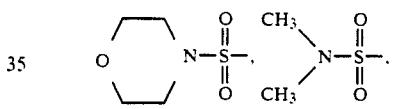

and X is PHE, NAPHTHYLALA or TYR(OMe).

Still other preferred compounds of the present invention are those of formula I wherein W is

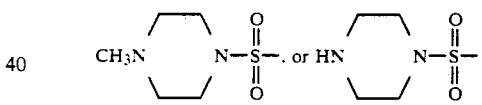

wherein $R_{10}$ is cyclohexyl or cyclohexylmethyl.

Particularly preferred compounds falling within the scope of the invention include the following compounds, their isomers, and pharmaceutically acceptable acid addition salts.

BOC—PHE—NHCH(CO$_2$CH$_3$)CO—CAD.

BMA—PHE—NHCH(CO$_2$CH$_3$)CO—CAD.

$\text{CH}_3\text{N}\underset{\underset{}{}}{\overset{}{\diagdown}}\text{N}-\underset{\underset{O}{\parallel}}{\overset{O}{\overset{\parallel}{S}}}-\text{NAPHTHYLALA}-\text{NHCH(CO}_2\text{CH}_3\text{)CO}-\text{CAD,}$

BOC—NAPHTHYLALA—NHCH(CO$_2$CH$_3$)CO—CAD, (CH$_3$)$_2$N—S(O)$_2$—NAPHTHYLALA—NHCH(CO$_2$CH$_3$)CO—CAD,

BMA—NAPHTHYLALA—NHCH(CO$_2$CH$_3$)CO—CAD,

IVA—NAPHTHYLALA—NHCH(CO$_2$CH$_3$)CO—CAD,

HN(piperazine)—S(O)$_2$—TYR(OMe)—NHCH(CO$_2$CH$_3$)CO—CAD,

CH$_3$N(piperazine)—S(O)$_2$—TYR(OMe)—NHCH(CO$_2$CH$_3$)CO—CAD,

BOC—TYR(OMe)—NHCH(CO$_2$CH$_3$)CO—CAD,

IVA—TYR(OMe)—NHCH(CO$_2$CH$_3$)CO—CAD,

BMA—TYR(OMe)—NHCH(CO$_2$CH$_3$)CO—CAD.

O(morpholine)—S(O)$_2$—PHE—NHCH(CO$_2$Et)CO—CAD,

HN(piperazine)—S(O)$_2$—PHE—NHCH(CO$_2$Et)CO—CAD,

CH$_3$N(piperazine)—S(O)$_2$—PHE—NHCH(CO$_2$Et)CO—CAD, (CH$_3$)$_2$N—S(O)$_2$—PHE—NHCH(CO$_2$Et)CO—CAD, BOC—PHE—NHCH(CO$_2$Et)CO—CAD.

IVA—PHE—NHCH(CO$_2$Et)CO—CAD,

BMA—PHE—NHCH(CO$_2$Et)CO—CAD,

O(morpholine)—S(O)$_2$—NAPHTHYLALA—NHCH(CO$_2$Et)CO—CAD,

HN(piperazine)—S(O)$_2$—NAPHTHYLALA—NHCH(CO$_2$Et)CO—CAD,

CH$_3$N(piperazine)—S(O)$_2$—NAPHTHYLALA—NHCH(CO$_2$Et)CO—CAD, (CH$_3$)$_2$N—S(O)$_2$—NAPHTHYLALA—NHCH(CO$_2$Et)CO—CAD, BOC—NAPHTHYLALA—NHCH(CO$_2$Et)CO—CAD, IVA—NAPHTHYLALA—NHCH(CO$_2$Et)CO—CAD, BMA—NAPHTHYLALA—NHCH(CO$_2$Et)CO—CAD, HN(piperazine)—S(O)$_2$—TYR(OMe)—NHCH(CO$_2$Et)CO—CAD, O(morpholine)—S(O)$_2$—TYR(OMe)—NHCH(CO$_2$Et)CO—CAD, CH$_3$N(piperazine)—S(O)$_2$—TYR(OMe)—NHCH(CO$_2$Et)CO—CAD, (CH$_3$)$_2$N—S(O)$_2$—TYR(OMe)—NHCH(CO$_2$Et)CO—CAD, BOC—TYR(OMe)—NHCH(CO$_2$Et)CO—CAD, IVA—TYR(OMe)—NHCH(CO$_2$Et)CO—CAD.

BMA—TYR(OMe)—NHCH(CO₂Et)CO—CAD.
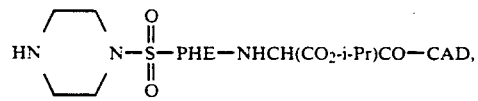
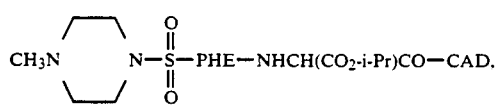
BOC—PHE—NHCH(CO₂-i-Pr)CO—CAD.
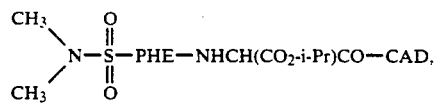
BMA—PHE—NHCH(CO₂-i-Pr)CO—CAD.
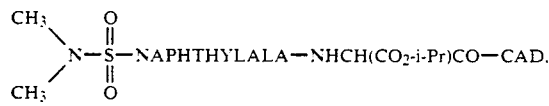
BOC—NAPHTHYLALA—NHCH(CO₂-i-Pr)CO—CAD.
IVA—NAPHTHYLALA—NHCH(CO₂-i-Pr)CO—CAD.
BMA—NAPHTHYLALA—NHCH(CO₂-i-Pr)CO—CAD.
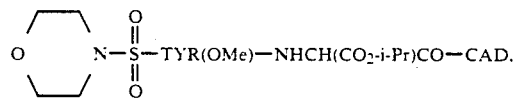
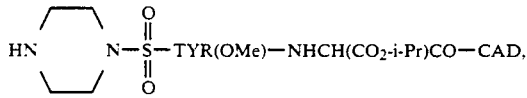
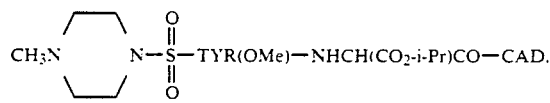
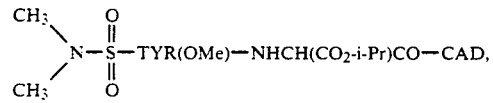
BOC—TYR(OMe)—NHCH(CO₂-i-Pr)CO—CAD.
IVA—TYR(OMe)—NHCH(CO₂-i-Pr)CO—CAD.
BMA—TYR(OMe)—NHCH(CO₂-i-Pr)CO—CAD.
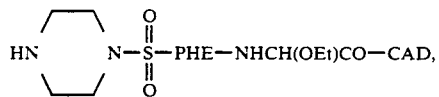
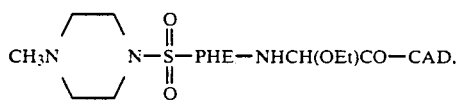
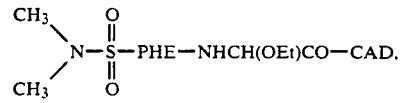
BOC—PHE—NHCH(OEt)CO—CAD,
BMA—PHE—NHCH(OEt)CO—CAD.
IVA—PHE—NHCH(OEt)CO—CAD,
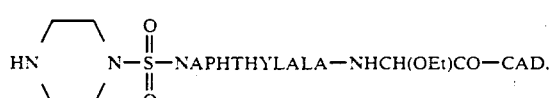

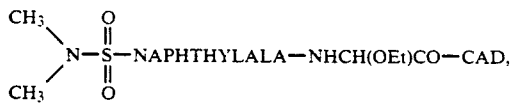
IVA—NAPHTHYLALA—NHCH(OEt)CO—CAD.
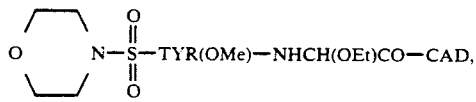
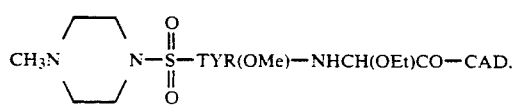
BOC—TYR(OMe)—NHCH(OEt)CO—CAD.
BMA—TYR(OMe)—NHCH(OEt)CO—CAD.
BOC—NAPHTHYLALA—NHCH(OEt)CO—CAD.
BMA—NAPHTHYLALA—NHCH(OEt)CO—CAD.
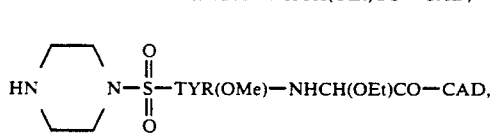
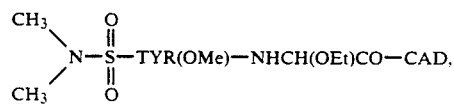
IVA—TYR(OMe)—NHCH(OEt)CO—CAD.
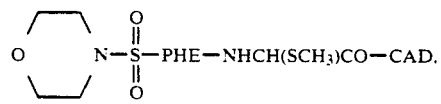
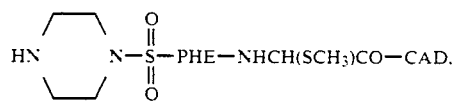
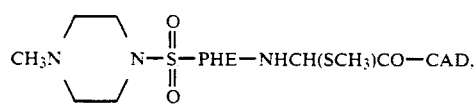
BOC—PHE—NHCH(SCH₃)CO—CAD.
IVA—PHE—NHCH(SCH₃)CO—CAD.
BMA—PHE—NHCH(SCH₃)CO—CAD.
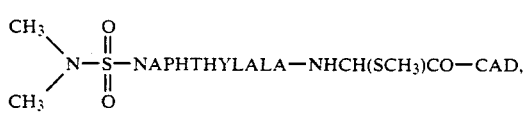
BOC—NAPHTHYLALA—NHCH(SCH₃)CO—CAD,
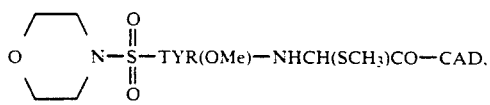
IVA—NAPHTHYLALA—NHCH(SCH₃)CO—CAD.
BMA—NAPHTHYLALA—NHCH(SCH₃)CO—CAD.
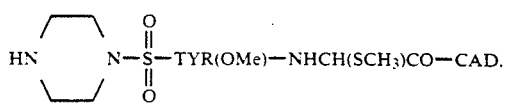

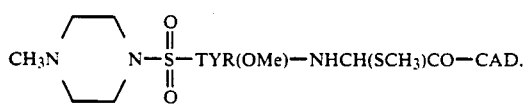
BOC—TYR(OMe)—NHCH(SCH₃)CO—CAD.
BMA—TYR(OMe)—NHCH(SCH₃)CO—CAD,
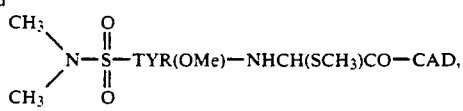
IVA—TYR(OMe)—NHCH(SCH₃)CO—CAD.
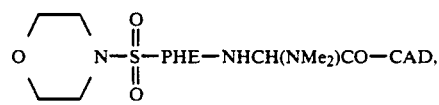
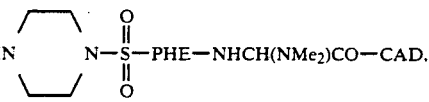
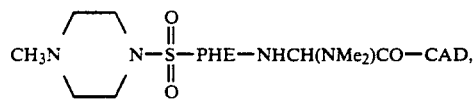
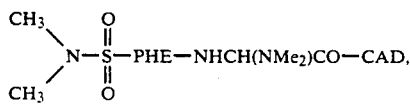
BOC—PHE—NHCH(NMe₂)CO—CAD,
IVA—PHE—NHCH(NMe₂)CO—CAD,
BMA—PHE—NHCH(NMe₂)CO—CAD,
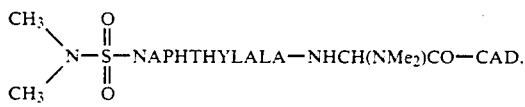
BOC—NAPHTHYLALA—NHCH(NMe₂)CO—CAD,
IVA—NAPHTHYLALA—NHCH(NMe₂)CO—CAD.
BMA—NAPHTHYLALA—NHCH(NMe₂)CO—CAD,
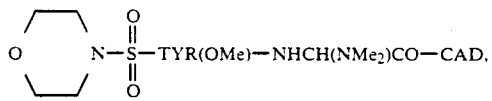
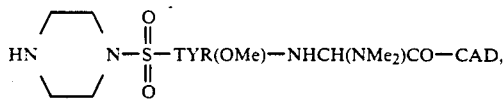
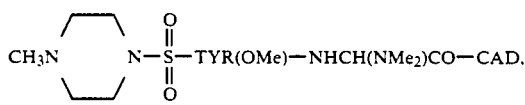
BOC—TYR(OMe)—NHCH(NMe₂)CO—CAD,
IVA—TYR(OMe)—NHCH(NMe₂)CO—CAD,
BMA—TYR(OMe)—NHCH(NMe₂)CO—CAD,
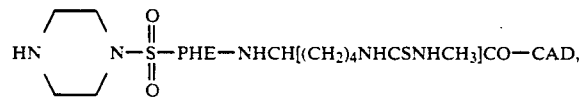

-continued

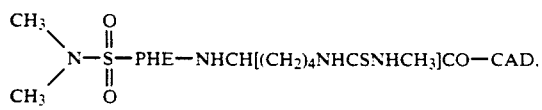          BOC—PHE—NHCH[(CH₂)₄NHCSNHCH₃]CO—CAD.

IVA—PHE—NHCH[(CH₂)₄NHCSNHCH₃]CO—CAD.          BMA—PHE—NHCH[(CH₂)₄NHCSNHCH₃]CO—CAD.

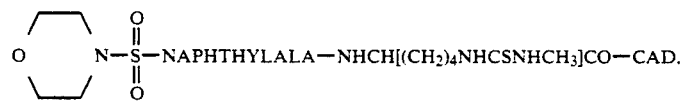

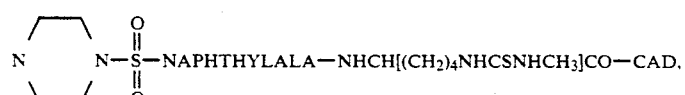

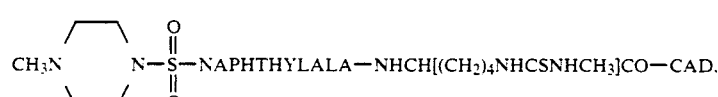

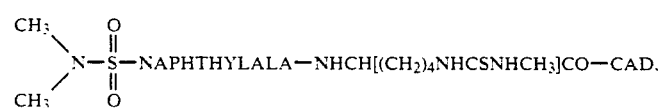

BOC—NAPHTHYLALA—NHCH[(CH₂)₄NHCSNHCH₃]CO—CAD.

IVA—NAPHTHYLALA—NHCH[(CH₂)₄NHCSNHCH₃]CO—CAD.

BMA—NAPHTHYLALA—NHCH[(CH₂)₄NHCSNHCH₃]CO—CAD.

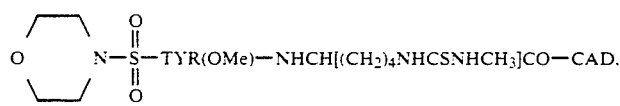

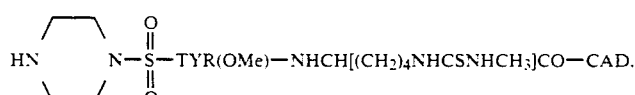

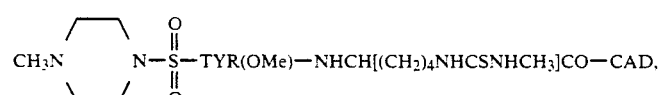

BOC—TYR(OMe)—NHCH[(CH₂)₄NHCSNHCH₃]CO—CAD.          IVA—TYR(OMe)—NHCH[(CH₂)₄NHCSNHCH₃]CO—CAD.

BMA—TYR(OMe)—NHCH[(CH₂)₄NHCSNHCH₃]CO—CAD.          BNMA—NHCH(CO₂CH₃)CO—CAD.

BNMA—NHCH(CO₂Et)CO—CAD.          BNMA—NHCH(CO₂-i-Pr)CO—CAD.

BNMA—NHCH(OEt)CO—CAD.          BNMA—NHCH(SCH₃)CO—CAD.

BNMA—NHCH(NMe₂)CO—CAD.          BNMA—NHCH[(CH₂)₄NHCSNHCH₃]CO—CAD.

-continued
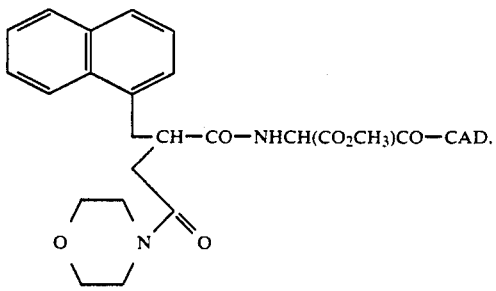
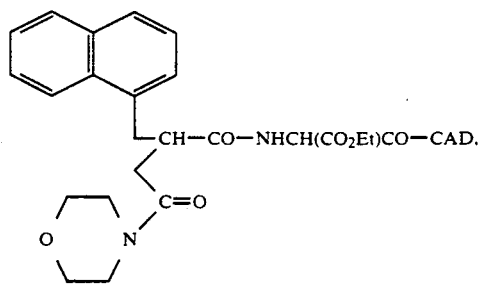
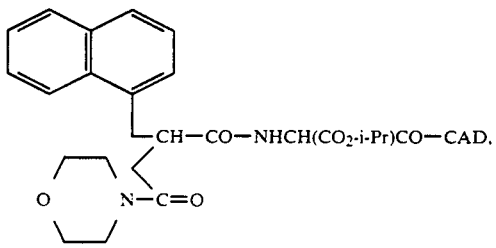
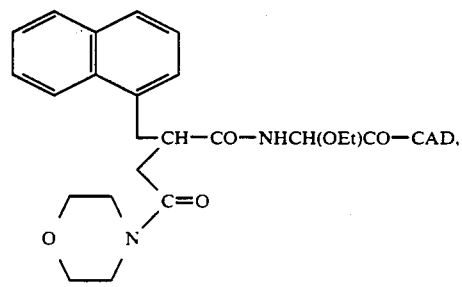
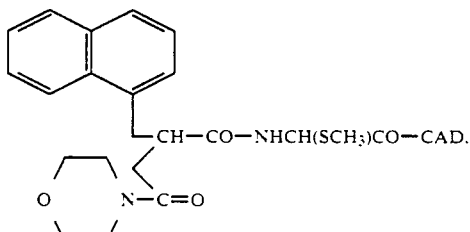
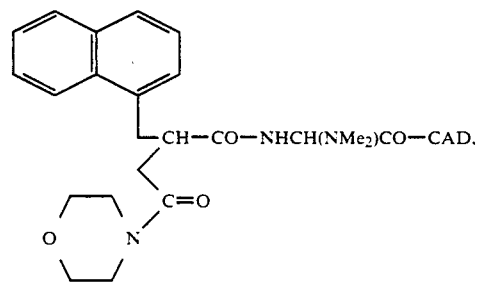
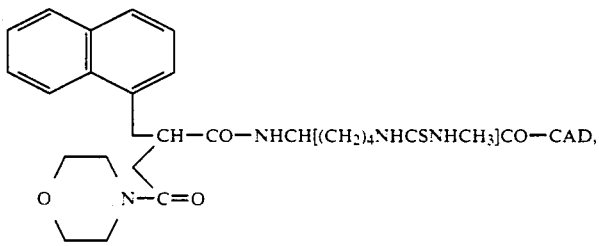
BBSP—TZA—CAD.
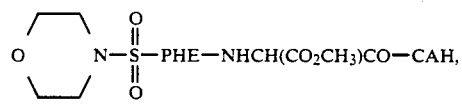
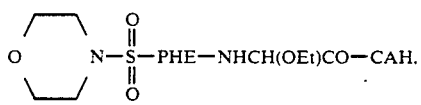
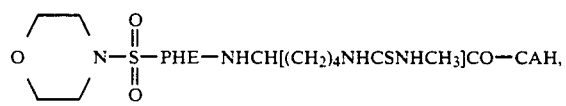
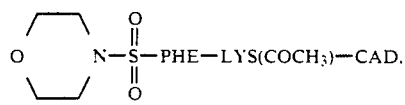
BMA—PHE—LYS(COCH₃)—CAD.
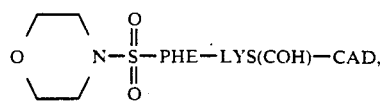
BMA—TYR(OMe)—LYS(COCH₃)—CAD.

-continued
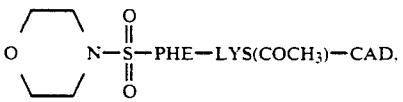
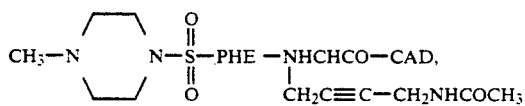
BMA—PHE—NHCHCO—CAD,
          |
          CH₂C≡C—CH₂NHCOCH₃
BBSP—LYS(COCH₃)—CAD,
BBSP—NHCH(CO₂C₂H₅)CO—CAD,
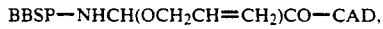
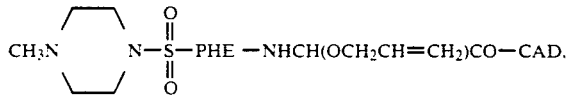
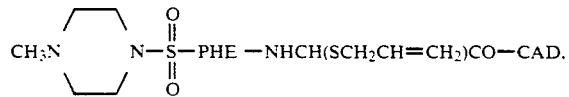
BMA—PHE—NHCH(SCH₂CH=CH₂)CO—CAD,
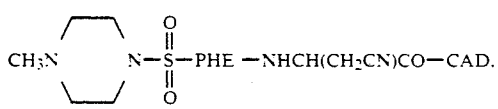
BBSP—NHCH(CH₂CN)CO—CAD,
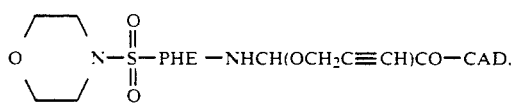
BMA—PHE—NHCH(OCH₂C≡CH)CO—CAD,
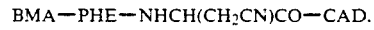
BMA—PHE—NHCH(OCH₂CH=CH₂)CO—CAD,
BMA—PHE—NHCH(CH₂CN)CO—CAD.
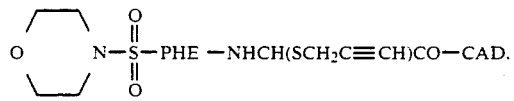
BMA—PHE—NHCH(SCH₂C≡CH)CO—CAD,
BBSP—NHCH(SCH₂C≡CH)CO—CAD.
and BBSP—NHCH(OCH₂C≡CH)CO—CAD,
Most preferred compounds are:
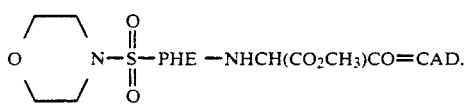
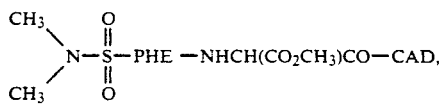
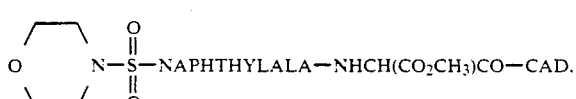
BBSP—HIS—CAD (slow isomer).

-continued
BBSP—HIS—CAD (fast isomer).
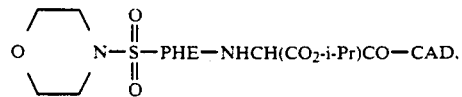
IVA—PHE—NHCH(CO₂CH₃)CO—CAD.
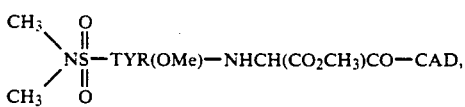
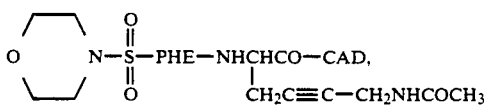
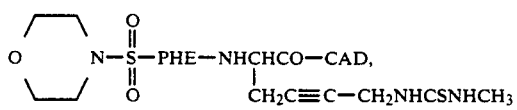
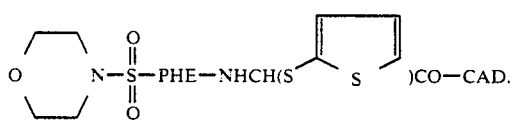
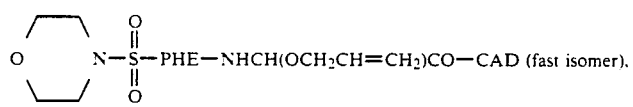
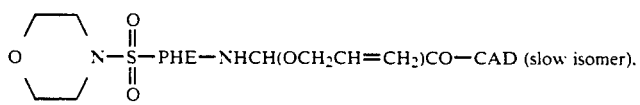
BMA—PHE—NHCH(OEt)CO—CAD.
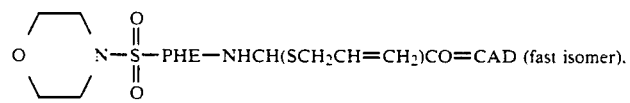
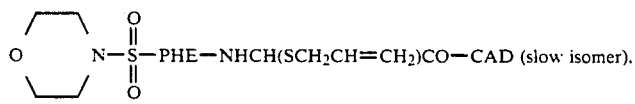
BOC—PHE—NHCH(SEt)CO—CAD (fast isomer).    BOC—PHE—NHCH(SEt)CO—CAD (slow isomer),
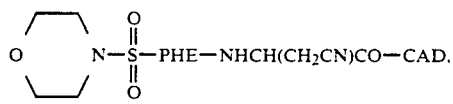      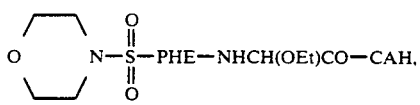
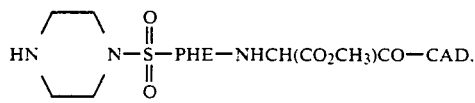      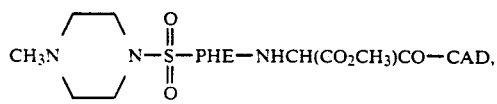
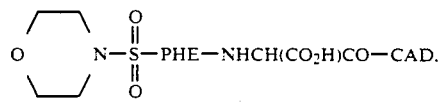      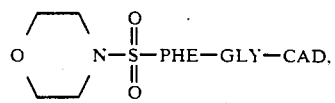

-continued

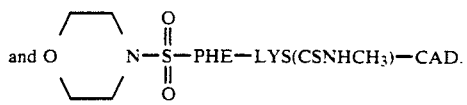

The compounds of the present invention have the advantage of increased hydrophilicity. This property makes the compounds more readily absorbed. Compounds of the invention have demonstrated in vivo activity.

The compounds include solvates and hydrates and pharmaceutically acceptable acid addition salts of the basic compounds of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) or S(L) configuration. The present invention includes all enantiomeric and epimeric forms as well as the appropriate mixtures thereof. Additionally, the preferred stereochemistry for W is as depicted below.

$$-NH-\underset{R_{10}}{\overset{(S)}{CH}}-\underset{(R)}{\overset{OH}{CH}}-\underset{(S)}{\overset{OH}{CH}}-CH_2CH(CH_3)_2$$

wherein $R_{10}$ is as defined above.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular final product desired.

The following scheme illustrates novel methods of preparing certain peptides of the present invention.

Scheme I

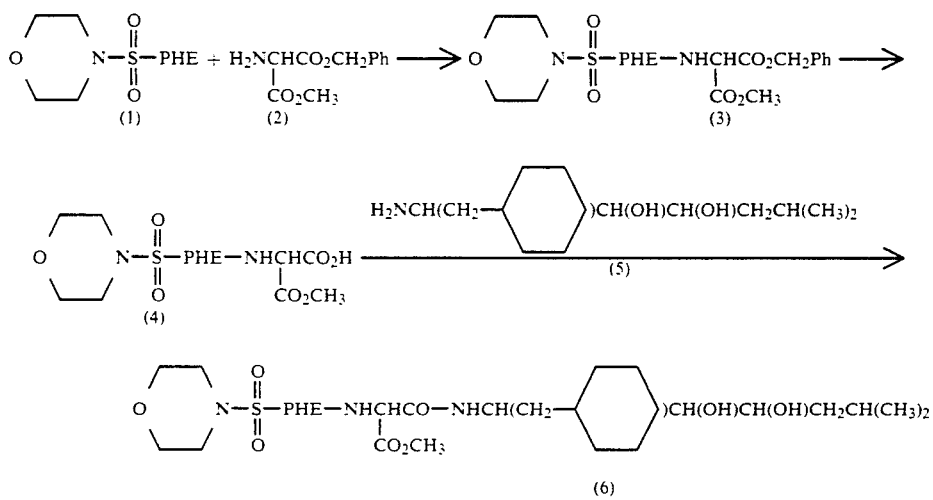

According to Scheme I above, morpholinosulfamylphenyl alanine (1) is reacted with amino malonate methyl benzyl ester (2) to form the diester (3). The reaction takes place in an inert solvent such as methylene chloride or DMF with hydroxybenzotriazole and dicyclohexylcarbodiimide at temperatures from 0° C. to 25° C.

The benzyl ester (3) is reacted with hydrogen gas in the presence of a catalyst such as 10% on palladium on charcoal to afford the carboxylic acid (4). The reaction takes place in a solvent such as methanol.

The carboxylic acid (4) is then reacted with amine (5) in an inert solvent such as methylene chloride or DMF with HOBT and DCC at temperatures from 0° C. to 25° C. to form (6), a compound of the present invention.

Scheme II

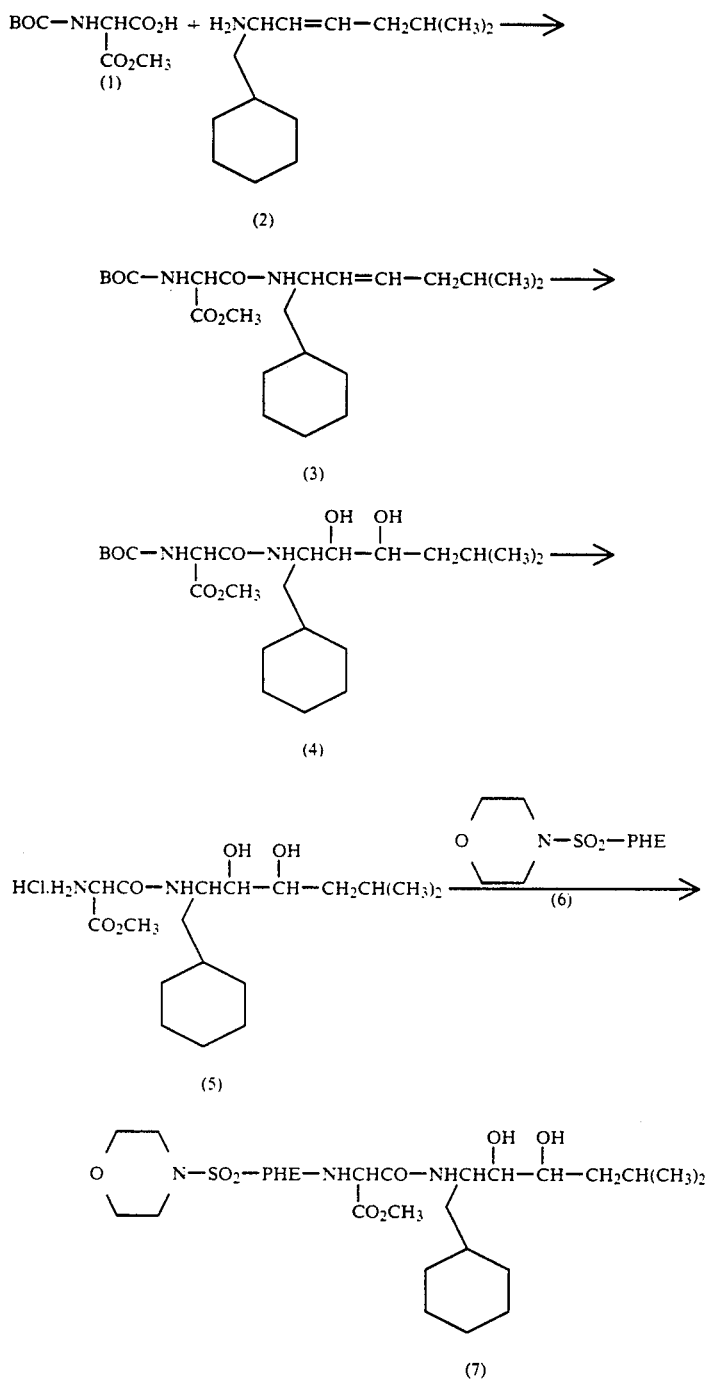

According to Scheme II above, methyl BOC-aminomalonate (1) is reacted with the unsaturated amine (2) to form (3). The reaction takes place in an inert solvent such as DMF, $CH_2Cl_2$, or THF with HBT and DCC at temperatures from 0° C. to 25° C.

Compound (3) is hydrozylated to compound (4) in THF using N-methyl-morpholine-N-oxide and catalytic amounts of osium tetroxide. The reaction is run at room temperature for one to three days.

Removal of the BOC-group to give (5) can be accomplished with HCl gas in $CH_2cl_2$ or $CHCl_3$ at room temperature for one to four hours.

coupling with

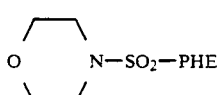

(6)

to give (7) is accomplished in an inert solvent such as DMF, $CH_2Cl_2$, or THF using an organic base such as $Et_3N$ to neutralize the HCl salt present. The coupling is accomplished with DCC and HOBT at temperatures from 0° C. to 25° C.

3) The active ester method—described in Chapter 3 of the above reference.

Scheme III

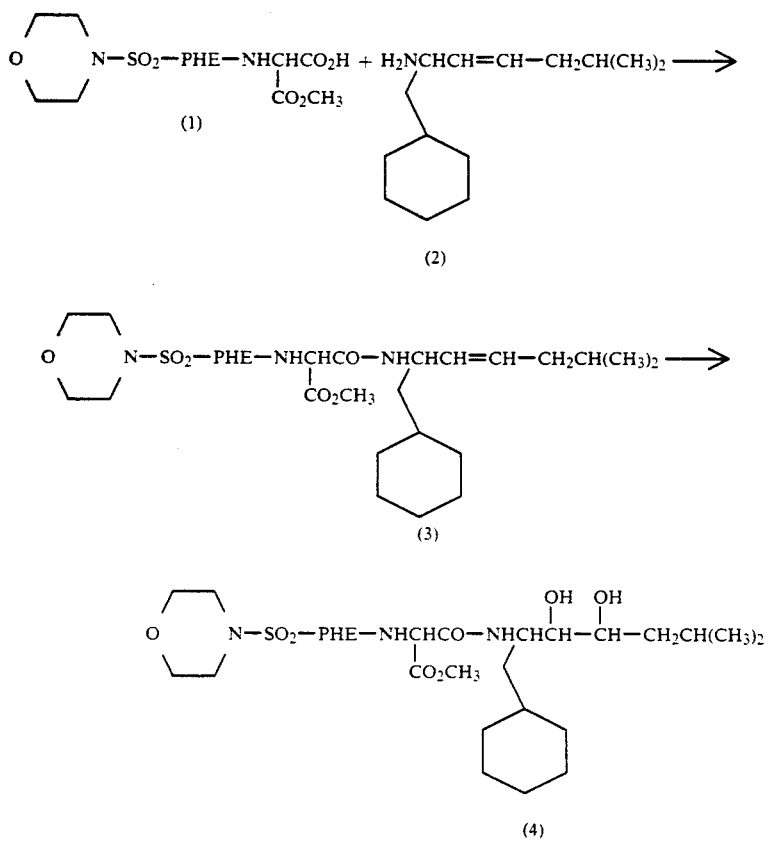

According to Scheme III above, reaction of (1) with (2) in an inert solvent such as DMF, CH$_2$Cl$_2$, or THF with DCC and HOBT at temperatures from 0° C. to 25° C. gives (3).

Compound (3) is hydroxylated to (4) in THF using N-methylmorpholine-N-oxide and a catalytic amount of osmium tetroxide. The reaction is run at room temperature for one to three days.

The strategy of peptides chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, NY, 1979, Vol. 1, pp. 42-44.

The DCC/HOBT method of coupling is well-known to those skilled in the art and is discussed in Chapter 5, "The Carbodiimide Method" by D.H. Rich and J. Singh in "The Peptides. Analysis, Synthesis, Biology," E. Gross and J. Meienhofer, Eds., Academic Press, New York, NY, 1979, Vol. 1, pp. 241-261.

Peptide coupling depends on activating the carboxy terminus of the amino protected amino acid and condensing it with another peptide containing a free amino terminus. In addition to the DCC coupling method described above, other methods of activating the carboxyl group of a protected amino acid include:

1) The azide method—described in Chapter 4 of the above reference.
2) The mixed anhydride method—described in Chapter 6 of the above reference.

The term lower alkyl refers to straight or branched chain alkyl radicals containing from 1 to 6 carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl, and the like.

Aryl means phenyl, naphthyl or other aromatic groups, including mono- or bicyclic, which may be substituted, especially monosubstituted, by F, Cl, Br, I, CF$_3$, OH, OR, or R, wherein R is lower alkyl.

Heteroaryl means aromatic heterocyclic rings containing at least one heteroatom selected from O, S, and N and from 3 to 5 carbon atoms including but not limited to thiazoles and imidazoles.

Aralkyl is as described above for alkyl and aryl, including but not limited to benzyl.

The compounds of the present invention are useful for treating renin-associated hypertension, congestive heart failure, and hyperaldosteronism. They are also useful as diagnostic tools for determining the presence of renin-associated hypertension or hyperaldosteronism.

Pharmaceutical compositions which comprise an effective amount of the compound in combination with a pharmaceutically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

An additional aspect of the present invention is a method for treating congestive heart failure in a mammal which comprises administering a pharmaceutical composition containing an effective amount of a compound in combination with a pharmaceutically acceptable carrier to the mammal.

Yet another aspect of the present invention is a process for preparing a compound of formula I wherein Y is

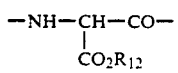

wherein $R_{12}$ is hydrogen lower alkyl, alkenyl, alkynyl or aralkyl which comprises:
a) reacting an N-sulfamyl amino acid with a primary amine to form the corresponding N-sulfamyl benzyl methyl ester;
b) by reacting the N-sulfamyl benzyl methyl ester with hydrogen gas in the presence of a catalyst to form the corresponding N-sulfamyl methyl ester acid; and
c) reacting the N-sulfamyl methyl ester acid with the appropriate free amine to form a desired compound of claim 1, formula I;
d) optionally hydrolyzing the methyl ester to the free acid o form a desired compound of claim 1, formula I.

yet another aspect of the instant invention is a process for preparing a compound of formula I wherein Y is

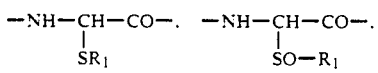

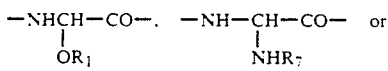

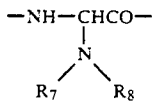

wherein $R_1$ is lower alkyl, alkenyl, alkynyl, aryl, heteroaryl, aralkyl, $(CH_2)_n$—$NHR_2$, wherein n is an integer of from 2 to 4,

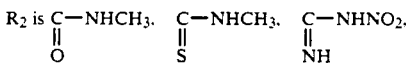

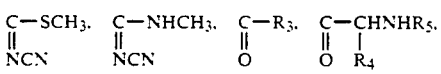

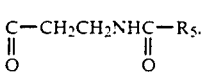

$R_3$ is hydrogen, lower alkylm or aryl, $R_4$ is lower alkyl or aralkyl, $R_5$ is

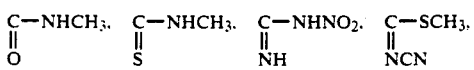

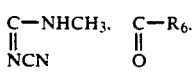

$R_6$ is hydrogen, lower alkyl or aryl, $R_7$ is $RR_1$,

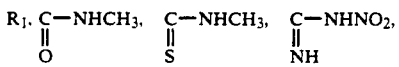

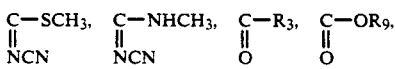

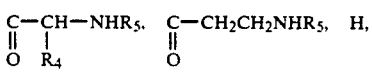

H, $R_8$ is lower alkyl or together with $R_7$, when $R_7$ is lower alkyl, forms a heterocyclic ring containing from 4 to 6 carbon atoms optionally containing one or more S, O, or NR; $R_9$ is alkyl or aralkyl; $R_{12}$ is lower alkyl or aralkyl, which comprises:
(a) reacting morpholinosulfamyl-PHE-$NH_2$ with glyoxylic acid in acetone to produce morpholinosulfamyl-PHE-α-hydroxy glycine;
(b) reacting the morpholinosulfamyl-PHE-α-hydroxy-glycine in ethanol-sulfuric acid to produce morpholinosulfamyl-PHE-α-ethoxyglycine, ethyl ester;
(c) or optionally reacting the clycine of a) above with ethanethiol in the presence of HOAc—$H_2SO_4$ to produce

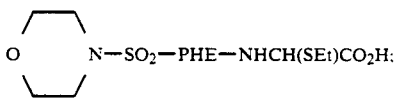

(d) hydrolyzing the ethyl ester of b) above in the presence of base to produce morpholinosulfamoyl-PHE-αethoxyglycine; and
(e) reacting the products of (c) or (d) above with the appropriate free amine to produce the desired compound of claim 1, formula I.

Yet another aspect of the instant invention is a process for preparing a compound of formula I wherein Y is

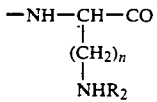

wherein n is an integer of from 2 to 4 and $R_2$ is

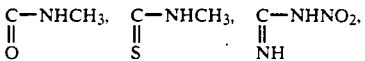

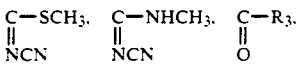

-continued $$-\underset{O}{\underset{\|}{C}}-\underset{R_4}{\underset{|}{CHNHR_5}}, \quad \underset{O}{\underset{\|}{C}}-CH_2CH_2\underset{O}{\underset{\|}{NHC}}-R_5.$$

$R_3$ is hydrogen, lower alkyl, or aryl, $R_4$ is H, lower alkyl or aralkyl, $R_5$ is $$\underset{O}{\underset{\|}{C}}-NHCH_3, \quad \underset{S}{\underset{\|}{C}}-NHCH_3, \quad \underset{NH}{\underset{\|}{C}}-NHNO_2, \quad \underset{NCN}{\underset{\|}{C}}-SCH_3,$$

$$\underset{NCN}{\underset{\|}{C}}-NHCH_3, \quad \underset{O}{\underset{\|}{C}}-R_6.$$

$R_6$ is hydrogen, lower alkyl or aryl, $R_7$ is $R_1$, $$R_1, \quad \underset{O}{\underset{\|}{C}}-NHCH_3, \quad \underset{S}{\underset{\|}{C}}-NHCH_3, \quad \underset{NH}{\underset{\|}{C}}-NHNO_2,$$

$$\underset{NCN}{\underset{\|}{C}}-SCH_3, \quad \underset{NCN}{\underset{\|}{C}}-NHCH_3, \quad \underset{O}{\underset{\|}{C}}-R_3, \quad \underset{O}{\underset{\|}{C}}-OR_9,$$

$$\underset{O}{\underset{\|}{C}}-\underset{R_4}{\underset{|}{CH}}-NHR_5, \quad \underset{O}{\underset{\|}{C}}-CH_2CH_2NHR_5, \quad H.$$

H, $R_8$ is lower alkyl, forms a heterocyclic ring containing from 4 to 6 carbon atoms optionally containing one or more S, O, or NR; $R_9$ is alkyl or aralkyl; $R_{12}$ is lower alkyl or aralkyl, which comprises:
(a) reacting BOC-LYS(Z) with 1-cyclohexyl-2-amino-3,4-didhydroxy-6-methylheptane to produce BOC-LYS(Z)-CAD,
(b) reacting BOC-LYS(Z)-CAD with a strong acid to produce LYS(Z)-CAD,
(c) coupling LYS(Z)-CAD with morpholinosulfamyl-PHE to produce morpholinosulfamyl-PHE-LYS(Z)-CAD,
(d) removing the Z from the product of step (c) above to produce morpholinosulfamyl-PHE-LYS-CAD, and
(e) reacting the product of step (d) above with the desired acylating agent to produce a desired compound of claim 1, formula I.

yet another aspect of the instant invention is a process for preparing a compound of formula I wherein Y is $$-NHCHCO- \atop \underset{CH_2CN}{|}$$

which comprises:
(a) treating Z-AZN is pyridine with DCC to give $$Z-NHCHCO_2H. \atop \underset{CH_2CN}{|}$$

(b) reacting $$Z-NHCHCO_2H \atop \underset{CH_2CN}{|}$$

with 1-cyclohexyl-2-amino-3,4-dihydroxy-6-methylheptane to produce $$Z-NHCHCO-CAD. \atop \underset{CH_2CN}{|}$$

(c) removing the Z-group with hydrogen in the presence of palladium on carbon to give $$H_2NCHCO-CAD, \atop \underset{CH_2CN}{|}$$

(d) coupling the product of c) above with morpholinosulfamyl-PHE using DCC to give a desired compound of formula I.

Yet another aspect of the instant invention is a process for preparing a compound of formula I wherein Y is $$-NHCHCO- \atop \underset{CH_2C\equiv C-CH_2NHR_2}{|}$$

wherein $R_2$ is $$\underset{O}{\underset{\|}{C}}-NHC_3, \quad \underset{S}{\underset{\|}{C}}-NHCH_3, \quad \underset{NH}{\underset{\|}{C}}-NHNO_2, \quad \underset{NCN}{\underset{\|}{C}}-SCH_3,$$

$$\underset{NCN}{\underset{\|}{C}}-NHCH_3, \quad \underset{O}{\underset{\|}{C}}-R_3, \quad \underset{O}{\underset{\|}{C}}-\underset{R_4}{\underset{|}{CHNHR_5}}.$$

$$\underset{O}{\underset{\|}{C}}CH_2CH_2\underset{O}{\underset{\|}{NHC}}-R_5.$$

$R_3$ is hydrogen, lower alkyl, or aryl, $R_4$ is H, lower alkyl, or aralkyl, $R_5$ is $$\underset{O}{\underset{\|}{C}}-NHCH_3, \quad \underset{S}{\underset{\|}{C}}-NHCH_3, \quad \underset{NH}{\underset{\|}{C}}-NHNO_2, \quad \underset{NCN}{\underset{\|}{C}}-SCH_3,$$

$$\underset{NCN}{\underset{\|}{C}}-NHCH_3, \quad \underset{O}{\underset{\|}{C}}-R_6.$$

$R_6$ is hydrogen, lower alkyl, or aryl, which comprises:
(a) reacting morpholinosulfamyl-PHE with diethyl aminomalonate·HCl in the presence of a coupling agent to give $$O\underset{\diagdown}{\diagup}N-SO_2-PHE-NHCH(CO_2Et)_2,$$

(b) alkylating the malonic ester with ClCH₂C≡C-CH₂NHBOC in the presence of NaH to give $$O\underset{\diagdown}{\diagup}N-SO_2-PHE-NHC(CO_2Et)_2 \atop \underset{CH_2C\equiv C-CH_2-NHBOC}{|}$$

(c) hydrolyzing the ester with NaOh and decarboxylating the malonic acid by heating in diozane/toluene to give

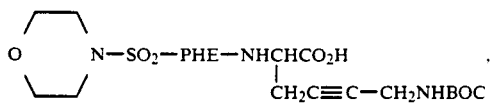

(d) coupling the product of (c) above with 1-cyclohexyl-2-amino-3,4-dihydroxy-6-methylheptane with DCC to give O⟨N⟩—SO₂—PHE—NHCHCO—CAD
                        |
                    CH₂C≡C—CH₂NHBOC (e) removing the BOC-group with HCl gas in dichloromethane to give

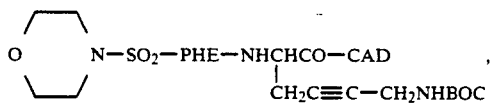

(f) reacting the product of (e) above with an appropriate acylating agent to give a desired compound of formula I.

Preferably in step (a) above the coupling agent is DCC.

The effectiveness of the aforementioned compounds is determined by a test for in vitro renin inhibitory activity. This activity is determined by a standard radioimmunoassay for angiotensin I. In this assay the enzyme, renin, incubated for two hours at 37° in the presence of a substrate, angiotensinogen, generates the product, angiotensin I. Test compounds are added to the incubation mixture. Relative activity is reported as the $IC_{50}$, which is the molar concentration of test compound causing a 50% inhibition of the renin activity.

TABLE II

| Compound | $IC_{50}$ (nM) |
|---|---|
| O⟨N⟩NS(O)(O)—PHE—NHCH(CO₂CH₃)CO—CAD | 0.14 |
| O⟨N⟩NS(O)(O)—PHE—NHCH(CO₂-i-Pr)CO—CAD | 0.68 |
| O⟨N⟩NS(O)(O)—PHE—NHCH(OEt)CO—CAD (fast isomer) | 0.25 |
| O⟨N⟩NS(O)(O)—PHE—NHCH(OEt)CO—CAD (slow isomer) | 1.4 |
| (CH₃)₂NS(O)(O)—TYR(OMe)—NHCH(CO₂CH₃)CO—CAD | 0.68 |
| O⟨N⟩NS(O)(O)—NAPHTHYLALA—NHCH(CO₂CH₃)CO—CAD | 0.6 |
| (CH₃)₂NS(O)(O)—PHE—NHCH(CO₂CH₃)CO—CAD | 0.66 |
| IVA—PHE—NHCH(CO₂CH₃)CO—CAD | 1.4 |
| O⟨N⟩N—S(O)(O)—TYR(OMe)—NHCH(CO₂CH₃)CO—CAD | 0.45 |
| BBSP—HIS—CAD (slow isomer) | 0.8 |
| BBSP—HIS—CAD (fast isomer) | 160 |

TABLE II-continued

| Compound | IC$_{50}$ (nM) |
|---|---|
| O⟨N-morpholino⟩-SO$_2$-PHE-NHCHCO-CAD, side chain CH$_2$C≡C-CH$_2$NHCOCH$_3$ | 7.6 |
| O⟨N-morpholino⟩-SO$_2$-PHE-NHCHCO-CAD, side chain CH$_2$C≡C-CH$_2$NHCOH | 6.0 |
| O⟨N-morpholino⟩-SO$_2$-PHE-NHCHCO-CAD, side chain CH$_2$C≡C-CH$_2$NHCSNHCH$_3$ | 24.0 |
| O⟨N-morpholino⟩-SO$_2$-PHE-NHCH(SEt)CO-CAD (fast isomer) | 0.13 |
| O⟨N-morpholino⟩-SO$_2$-PHE-NHCH(SEt)CO-CAD (slow isomer) | 18.0 |
| O⟨N-morpholino⟩-SO$_2$-PHE-NHCHCO-CAD, side chain dithiolane (S-S) | 13.0 |
| O⟨N-morpholino⟩-SO$_2$-PHE-NHCH(OCH$_2$CH=CH$_2$)CO-CAD (fast isomer) | 0.045 |
| O⟨N-morpholino⟩-SO$_2$-PHE-NHCH(OCH$_2$CH=CH$_2$)CO-CAD (slow isomer) | 1.1 |
| BMA-PHE-NHCH(OEt)CO-CAD | 1.4 |
| O⟨N-morpholino⟩-SO$_2$-PHE-NHCH(SCH$_2$CH=CH$_2$)CO-CAD (fast isomer) | 0.17 |
| O⟨N-morpholino⟩-SO$_2$-PHE-NHCH(SCH$_2$CH=CH$_2$)CO-CAD (slow isomer) | 38.0 |
| BOC-PHE-NHCH(SEt)CO-CAD (fast isomer) | 1.4 |
| BOC-PHE-NHCH(SEt)CO-CAD (slow isomer) | >10.0 |
| O⟨N-morpholino⟩-SO$_2$-PHE-NHCH(CH$_2$CN)CO-CAD | 0.4 |
| O⟨N-morpholino⟩-SO$_2$-PHE-NHCH(OEt)CO-CAH | 25.0 |

TABLE II-continued

| Compound | IC$_{50}$ (nM) |
|---|---|
| HN⟨ ⟩N—S(=O)$_2$—PHE—NHCH(CO$_2$CH$_3$)CO—CAD | 0.6 |
| CH$_3$N⟨ ⟩N—S(=O)$_2$—PHE—NHCH(CO$_2$CH$_3$)CO—CAD | 0.3 |
| O⟨ ⟩N—S(=O)$_2$—PHE—NHCH(CO$_2$H)CO—CAD | 12.0 |
| O⟨ ⟩N—S(=O)$_2$—PHE—GLY—CAD | 5.0 |
| O⟨ ⟩N—S(=O)$_2$—PHE—LYS(CSNHCH$_3$)—CAD | 0.19 |

When

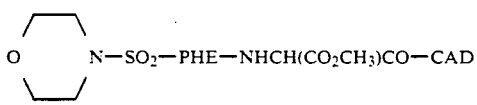

was administered orally at 10 or 30 mg/kg to high renin hypertensive Cynomolgus monkeys, it showed a does dependent reduction in blood pressure. At 30 kg/mg PO it showed a 24 mm Hg reduction in blood pressure two hours post dose. The plasma renin activity at this time was inhibited by >98%.

As can be seen from the above results, the compounds of the present invention have a significant effect on the activity of renin and thus are useful for the treatment of hypertension, hyperaldosteronism, and congestive heart failure.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powder and tablets preferably contain from 5 to 10 to about 70 percent of the active ingredient. Suitable solid carriers are magnesium carbonate, magnesium stearate, talc, sugar, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powers, cachets, and capsules can be used as solid dosage forms suitable for oral administration.

The compound of the present invention may be administered orally, buccally, parenterally, by inhalation spray, rectally, or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection, or infusion techniques.

For preparing suppositories, a low melting wax such as a mixture of fatty acid gycerides or cocoa butter is first melted, and the active ingredient is dispersed homogeneously therein by stirring. The molten homogeneous mixture is then poured into convenient sized molds, allowed to cool, and thereby solidify Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcelulose, sodium carboxymethylcelulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dosage form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg/kg of body weight per day or preferably 25 to 750 mg/kg of body weight per day optionally in divided portions. The dosages, however, per day may be varied depending upon the requirements of the patient, the severity of the condition being treated and the compound being employed. Determination of the proper dosage for a particular situation is within the skill of the art. Generally, treatment is initiated with small dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

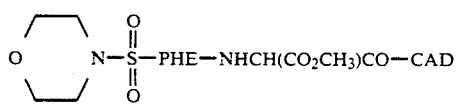

A mixture of morpholinosulfamyl-PHE-NHCH(CO₂CH₃)CO₂H (0.5 g), DCC (0.25 g), HOBT·H₂O (0.16 g) and 10 ml DMF is stirred at 25° for ten minutes. The resulting slurry is treated with a solution of

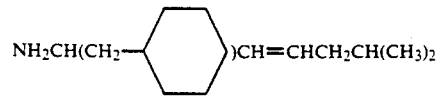

(0.30 g) in 5 ml DMF. After stirring at 25° for 24 hours the reaction is filtered and concentrated under vacuum. The residue is dissolved in CH₂Cl₂ (75 ml) and this solution is washed with 5% aqueous Na₂CO₃ (25 ml), dried over MgSO₄, and evaporated. The major product is isolated by flash chromatography on silica gel.

This produce (0.4 g) is dissolved in THF (10 ml) and N-methylmorpholine-N-oxide (0.22 g) and osmium tetroxide (0.01 g) is added. The reaction mixture is stirred for 72 hours and is filtered and concentrated under vacuum. The residue is dissolved in ethyl acetate (75 ml) and washed with 10% Na₂SO₃ (25 ml), 10% citric acid (25 ml), saturated aqueous NaHCO₃ (25 ml) and saturated aqueous NaCl (25 ml). The major product is isolated by flash chromatography on silica gel, eluting with CHCl₃—MeOH (99:1) to afford a crisp foam upon evaporation of solvents. MS (FAB) 655 (m+1). (FAB is fast atom bombardment).

EXAMPLE 2

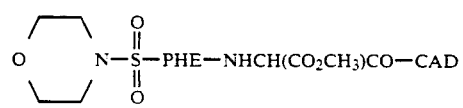

A mixture of morpholinosulfamyl-PHE-NHCH(CO₂CH₃)CO₂H (0.5 g), DCC (0.25 g), HOBT·H₂O (0.16 g) and 10 ml DMF was stirred at 25° for ten minutes. A solution of

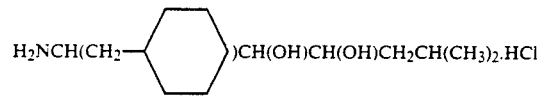

and N-methylmorpholine (0.15 ml) in 10 ml DMF was added to the slurry and stirred for 48 hours. The reaction was filtered and concentrated under vacuum. The residue was dissolved in EtOAc (200 ml) and this solution was washed with water (100 ml), saturated aqueous NaHCO₃ (100 ml), water (100 ml) and saturated sodium chloride (50 ml), dried over MgSO₄, and evaporated. The product was isolated by flash chromatography on silica gel. The structure was confirmed by NMR and mass spectroscopy.

Calcd. for C₃₁H₅₀N₄O₉S (MW 654.74: C, 56.86; H, 7.70; N, 8.56. Found: C, 56.44; H, 7.61; N, 8.86.

EXAMPLE 3

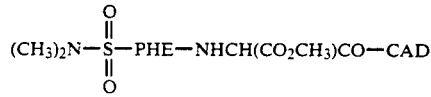

Substitution of dimethylsulfamyl-PHE-NHCH(CO₂CH₃)CH₂H for morpholinosulfamyl-PHE-NHCH(CO₂CH₃)CO₂H in Example 2 afforded the desired product whose structure was confirmed by NMR and mass spectroscopy.

Calcd. for $C_{29}H_{48}N_4OS$ (MW 612.71): C, 56.84; H, 7.90; N, 9.15. Found: C, 57.19; H, 8.20; N, 9.29.

EXAMPLE 4

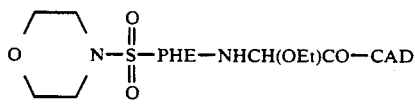

Substitution of morpholinosulfamyl-PHE-NHCH(O-Et)CO$_2$H for morpholinosulfamyl-PHE-NHCH(CO$_2$H in Example 2 afforded the desired product. Chromatography on silica gel, eluting with a gradient of 0–2% MeOH in CHCl$_3$, gave the fast moving diastereomer. The structure was confirmed by NMR and mass spectroscopy.

Calcd. for $C_{31}H_{52}N_4O_8S$ (MW 640.76): C, 58.10; H, 8.18; N, 8.74. Found: C, 58.12; H, 8.33; N, 8.43.

Continued elution from the column gave the slow moving diasteomer. The structure was confirmed by NMR and mass spectroscopy.

Calcd. for $C_{31}H_{52}N_4O_8S$ (MW 640.76): C, 58.10; H, 8.18; N, 8.74. Found: C58.60; H, 8.41; N, 8.56.

EXAMPLE 5

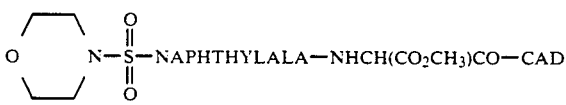

A mixture of morpholinosulfamyl-NAPHTHYLALA-NHCH(CO$_2$CH$_3$CO$_2$H (0.5 g), DCC (0.25 g), HOBT·H$_2$O (0.16 g) and 10 ml DMF is stirred at 25° for 10 minutes. The resulting slurry is treated with a solution of

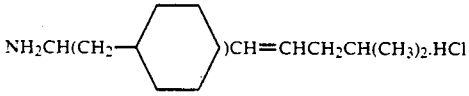

and N-methylmorpholine (0.15ml) in 10 ml DMF. After stirring at 25° for twenty-four hours the reaction is filtered and concentrated. The residue is dissolved in EtOAc (75 ml) and this solution is washed with 5% aqueous Na$_2$CO$_3$ (25 ml), dried over MgSO$_4$ and evaporated. The major product is isolated by flash chromatography on silica gel.

This product (0.4 g) is dissolved in THF (10 ml) and N-methylmorpholine-N-oxide (0.22 g) and osmium tetroxide (0.01 g) is added. The reaction mixture is stirred for seventy-two hours and is filtered and concentrated. The residue is dissolved in EtOAc (75 ml) and washed with 10% Na$_2$SO$_3$ (25 ml), 10% citric acid (25 ml), saturated aqueous NaHCO$_3$ and saturated aqueous sodium chloride (25 ml). The major product is isolated by flash chromotography on silica gel.

EXAMPLE 6

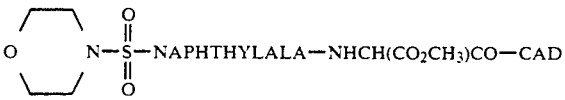

A solution of 560 mg (1.17 mmole) of morpholinosulfamyl-NAPHTHYLALA-NHCH(CO$_2$CH$_3$)CO$_2$H, 360 mg (1.29 mmole) of

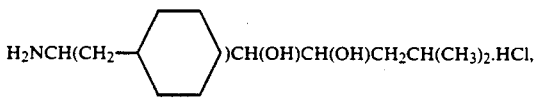

and 174 mg (1.29 mmole) of HOBT in 25 ml CH$_2$Cl$_2$ was treated with 0.24 ml (1.75 mmole) of Et$_3$N followed by 266 mg (1.29 mmole) of DCC and the mixture allowed to stir at room temperature overnight. The solvent was removed under reduced pressure and the residue taken up in ErOAc. After filtering, the EtOAc was washed with H$_2$O, saturated NaHCO$_3$, and saturated NaCl. Drying over MgSO$_4$ and removal of the solvent under reduced pressure gave the crude product which was purified b chromatography on silica gel, eluting with a gradient of 0–2% MeOH in CHCl$_3$. The structure of the product was confirmed by NMR and mass spectroscopy.

Calcd. for $C_{35}H_{52}N_4O_9S\cdot 0.1CHCl_3$ (MW 716.74): C, 58.82; H, 7.33; N, 7.82. Found: C, 58.75; H, 7.44; N, 7.57.

EXAMPLE 7

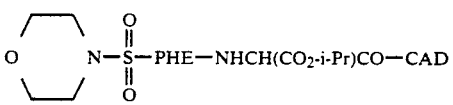

Substitution of morpholinosulfamyl-PHE-NHCH(CO$_2$—i Pr)CO$_2$H for morpholinosulfamyl-PHE-NHCH(CO$_2$CH$_2$)CO$_2$H in Example 2 afforded the desired product whose structure was confirmed by NMR and mass spectroscopy.

Calcd. for $C_{33}H_{54}N_4O_9S$ (MW 682.79): C, 58.05; H, 7.97; N, 8.21. Found: C, 58.04; H, 7.92; N, 7.99.

EXAMPLE 8

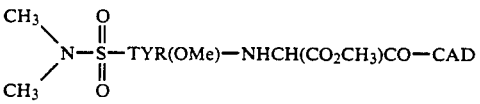

Substitution of dimethylsulfamyl-TYR(OMe) NHCH(CO$_2$CH$_3$)CO$_2$H for morpholinosulfamyl-NAPHTHYLALA NHCH(CO$_2$CH$_3$)CO$_2$H in Example 6 afforded the desired product whose structure was confirmed by NMR and mass spectroscopy.

Calcd. for $C_{30}H_{50}N_4O_9S$ (MW 642.73): C, 56.06; H, 7.84; N, 8.72. Found: C, 56.12; H, 7.81; N, 8.90.

EXAMPLE 9

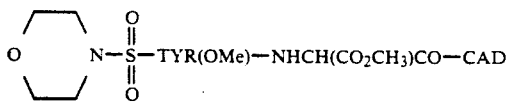

Substituting morpholinosulfamyl-TYR(OMe)-NHCH(CO$_2$CH$_3$)CO$_2$H for morpholinosulfamyl-PHE-NHCH(CO$_2$CH$_3$)CO$_2$H in Example 2 afforded the desired product which was purified by chromatography on silica gel, eluting with a gradient of 0-4% MeOH in CHCl$_3$. The structure was confirmed by NMR and mass spectroscopy.

Calcd. for C$_{32}$H$_{52}$N$_4$O$_{10}$S (MW 684.77): C, 56.12; H, 7.65; N, 8.18. Found: C, 55.82; H, 7.78; N, 8.24.

EXAMPLE 10

IVA-PHE-NHCH(CO$_2$CH$_3$)CO-CAD

Substituting IVA-PHE-NHCH(CO$_2$CH$_3$)CO$_2$H for morpholinosulfamyl-PHE-NHCH(CO$_2$CH$_3$)CO$_2$H in Example 2 afforded the desired product whose structure was confirmed by NMR and mass spectroscopy.

Calcd. for C$_{32}$H$_{51}$N$_3$O$_7$ (MW 589.75): C, 65.17; H, 8.72; N, 7.13. Found: C, 65.03; H, 8.68; N, 7.39.

EXAMPLE 11

BBSP-HIS-CAD (Isomer A)

A solution of 1.6 g (1.8 mmole) of BBSP-HIS(TRT)-CAD (fast moving isomer) in 100 ml of 80% HOAc was warmed on a steam bath for five minutes, then diluted with 200 ml of H$_2$O. After extracting with Et$_2$O, the aqueous solution was concentrated. The suspension obtained on diluting with H$_2$O was made basic with NaHCO$_3$, and extracted with CHCl$_3$. The CHCl$_3$ was washed with saturated NaCl and dried over Na$_2$SO$_4$. After removal of the solvent under reduced pressure, the residue was chromatographed on silica gel, eluting with a gradient of 0-4% MeOH in CHCl$_3$. There was obtained 0.53 g of pure product. This was converted to the methanesulfonic acid salt, dissolved in H$_2$O, and freeze-dried. The structure was confirmed by NMR and mass spectroscopy.

Calcd. for C$_{34}$H$_{54}$N$_4$O$_6$S·CH$_3$SO$_3$H·2.3H$_2$O (MW 784.28): C, 53.60; H, 8.05; N, 7.14. Found: C, 53.57; H, 7.83; N, 7.00

EXAMPLE 12

BBSP-HIS-CAD (Isomer) B

Using 2.2 g (2.48 mmole) of BBSP-HIS(TRT)-CAD (slow moving isomer) and proceeding as in Example 11, there was obtained 0.93 g of product. This was converted to the methanesulfonic acid salt, dissolved in H$_2$O, and freeze-dried. The structure was confirmed by NMR and mass spectroscopy.

Calcd. for C$_{34}$H$_{54}$N$_4$O$_6$S·CH$_3$SO$_3$H·1.6 H$_2$O (MW 771.67): C, 54.47; H, 7.99; N, 7.26. Found: C, 54.49; H, 7.88; N, 7.08.

EXAMPLE 13

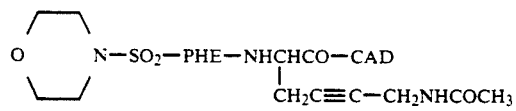

A solution of 1.35 g (2.0 mmole) of

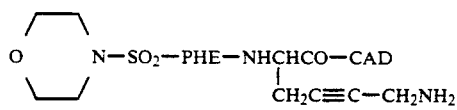

in 40 ml CH$_2$Cl$_2$ was cooled in ice and 250 mg (2.2 mmole) of acetylimidazole added, and the solution allowed to stir at room temperature overnight. The solvent was removed under reduced pressure and the residue taken up in EtOAc, and washed with 1N HCl, H$_2$O, saturated NaHCO$_3$, and saturated NaCl. Drying over MgSO$_4$ and removal of the solvent under reduced pressure gave the crude product which was purified by chromatography on silica gel, eluting with CHCl$_3$/MeOH (98/2). There was obtained 1.23 g of product as a white foam. The structure was confirmed by NMR and mass spectroscopy.

Calcd. for C$_{35}$H$_{55}$N$_5$O$_8$S 0.4CHCl$_3$ (MW 753.58): C, 56.42; H, 7.41; N, 9.29. Found: C$_{56.14}$, H, 7.53; N, 9.24.

EXAMPLE 14

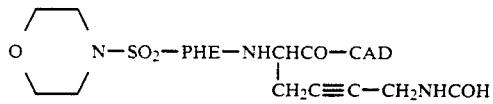

A solution of 1.35 g (2.0 mmole) of

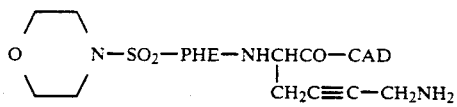

in 20 ml CH$_2$Cl$_2$ was cooled in ice and treated with 0.18 ml (2.0 mmole) of formic-acetic anhydride and 0.3 ml (2.0 mmole) of Et$_3$N, then allowed to stir at room temperature overnight. The solvent was removed under reduced pressure and the residue taken up in EtOAc and washed with 1N HCl, H$_2$O, saturated NaHCO$_3$, and saturated NaCl. Drying over MgSO$_4$ and removal of the solvent under reduced pressure left the crude product which was purified by chromatography on silica gel, eluting with CHCl$_3$/MeOH (98/2). There was obtained 1.06 g of product as a white foam. The structure was confirmed by NMR and mass spectroscopy.

Calcd. for C$_{34}$H$_{53}$N$_5$O$_8$S·0.45CHCl$_3$ (MW 745.53): C, 55.50; H, 7.23; N, 9.39. Found: C, 55.59; H, 7.29; N, 9.19

EXAMPLE 15

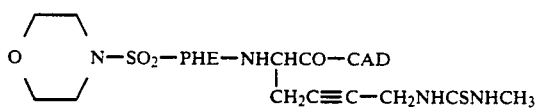

A solution of 1.35 g (2.0 mmole) of

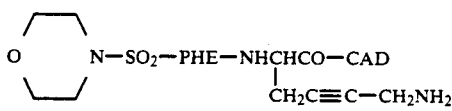

in 20 ml CH$_2$Cl$_2$ was cooled in ice and treated with 154 mg (2.1 mmole) of methyl isothiocyanate and 0.6 ml (4.2 mmole) of Et$_3$N and stirred at room temperature for three days. The solvent was removed under reduced pressure and the residue taken up in EtOAc and washed with 1n HCl, H$_2$O, saturated NaHCO$_3$, and saturated NaCl. Drying over MgSO$_4$ and removal of the solvent under reduced pressure left the crude product which was purified by chromatography on silica gel, eluting with CHCl$_3$/MeOH (98/2). There was obtained 810 mg of product as a pale yellow foam. The structure was confirmed by NMR and mass spectroscopy.

Calcd. for C$_{35}$H$_{56}$N$_6$O$_7$S$_2$.0.8CHCl$_3$ (MW 823.36): C, 51.66; H, 6.88; N, 10.11. Found: C, 51.85; H, 6.96; N, 10.08.

EXAMPLES 16 and 17

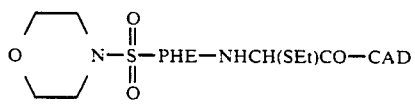

A solution of 3.3 g (7.7 mmole) of

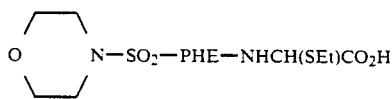

and 1.08 g (8.08 mmole) of HOBT in 100 ml CH$_2$Cl$_2$ was cooled in ice and 1.67 g (8.08 mmole) of DCC added, followed by a cold solution of 2.15 g (7.7 mmole) of

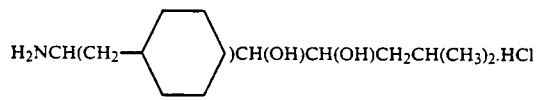

and 1.13 ml (8.08 mmole) of Et$_3$N in 30 ml CH$_2$Cl$_2$. After stirring at 22° overnight, the mixture was filtered and evaporated under reduced pressure to an oil. The oil was dissolved in EtOAc and washed with saturated NaCl, 1N citric acid, saturated NaCl, saturated NaHCO$_3$ and saturated NaCl. The organic phase was dried over MgSO$_4$ and evaporated to give the crude product as a foam, 5.22 g. Chromatography on silica gel, eluting with EtOAc/CHCl$_3$ (50/50) gave the faster eluting isomer as a crystalline solid. The solid was triturated with Et$_2$O and dried under vacuum, giving a white solid, 1.36 g. The structure was confirmed by NMR and mass spectroscopy.

Calcd. for C$_{31}$H$_{52}$N$_4$O$_7$S$_2$ (MW 656.91): C, 56.77; H, 7.84; N, 8.53. Found: C, 56.84; H, 7.96; N, 8.49.

Continued elution from the column gave the slower eluting isomer as a white solid, 1.49 g. The structure was confirmed by NMR and mass spectroscopy.

Calcd. for C$_{31}$H$_{52}$N$_4$O$_7$S$_2$ (MW 656.91): C, 56.77; H, 7.84; N, 8.53. Found: C, 56.58; H, 7.93; N, 8.47.

EXAMPLE 18

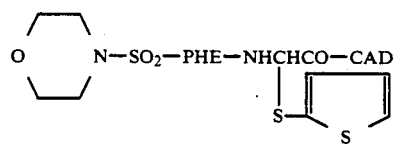

A solution of 2.42 g (4.97 mmole) of

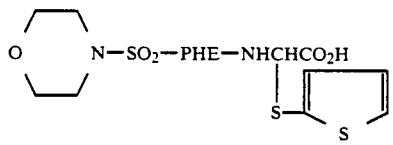

and 0.7 g (5.22 mmole) of HOBT in 80 ml CH$_2$Cl$_2$ and 5 ml DMF was cooled in ice and treated with 1.08 g (5.22 mmole) of DCC followed by a cold solution of 1.39 g (4.97 mmole) of

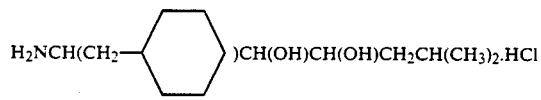

and 0.73 ml (5.22 mmole) of Et$_3$N in 20 ml CH$_2$Cl$_2$. After stirring at room temperature overnight, the mixture was filtered and the solvent removed under reduced pressure. The residue was taken up in EtOAc and washed with 1N citric acid, saturated NaCl, saturated NaHCO$_3$, and saturated NaCl. After drying over MgSO$_4$, the solvent was removed under reduced pressure to give 3.7 g of the crude product as a brown solid. Trituration with Et$_2$O left 2.3 g of partially purified product. Chromatography on silica gel, eluting with EtOAc/CHCl$_3$ (50/50) gave 2.05 g of the product as a white solid. The structure was confirmed by NMR and mass spectroscopy.

Calcd. for C$_{33}$H$_{50}$N$_4$O$_7$S$_3$ (MW 710.98): C, 55.75; H, 7.09; N, 7.88. Found: C, 55.95; H, 7.28; N, 7.87.

EXAMPLES 19 and 20

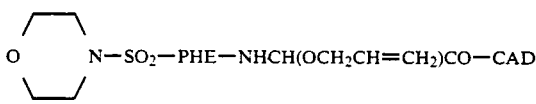

A solution of 1.91 g (4.47 mmole) of

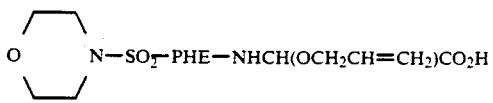

and 0.62 g (4.56 mmole) of HOBT in 40 ml CH$_2$Cl$_2$ and 5 ml DMF was cooled in ice and treated with 0.94 g (4.56 mmole) of DCC, followed by a cold solution of 1.25 g (4.47 mmole) of

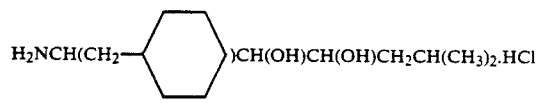

and 0.63 ml (4.56 mmole) of Et$_3$N in 15 ml CH$_2$Cl$_2$. After stirring at room temperature overnight, the mixture was filtered and the filtrate evaporated under reduced pressure. The residue was taken up in EtOAc, filtered, and washed with 1N citric acid, saturated NaCl, saturated NaHCO$_3$, and saturated NaCl. Drying over MgSO$_4$ and removal of the solvent under reduced pressure gave 2.8 g of the crude product as a foam. Chromatography on silica gel, eluting with EtOAc/CHCl$_3$ (50/50) gave the faster eluting isomer. Trituration with Et$_2$O gave 0.72 g of the product as a white solid. The structure was confirmed by NMR and mass spectroscopy.

Calcd. for C$_{32}$H$_{52}$N$_4$O$_8$S·0.5H$_2$O (MW 661.78): C, 58.16; H, 7.93; N, 8.48. Found: C, 57.98; H, 8.05; N, 8.41.

Further elution from the column gave the slower eluting isomer which still retained about 10% of the faster eluting isomer. Evaporation of an Et$_2$O solution gave 0.62 g of the product as a white foam. The structure was confirmed by NMR and mass spectroscopy.

Calcd. for C$_{32}$H$_{52}$N$_4$O$_8$S·0.5H$_2$O (MW 661.78): C, 58.07; H, 8.07; N, 8.47. Found: C, 58.11; H, 8.08; N, 8.29.

EXAMPLE 21

BMA-PHE-NHCH(OEt)CO-CAD

A solution of 1.58 g (2.18 mmole) of Z-BMA-PHE-NHCH(OEt)CO-CAD in 100 ml of EtOH was treated with 0.3 g of 20% Pd/C and the mixture purged with hydrogen for four hours. The mixture was filtered and the solvent removed under reduced pressure. The residue was triturated with Et$_2$O to give 1.2 g of a white solid. Chromatography on silica gel, eluting with a gradient of 0-15% MeOH in CHCl$_3$ gave 0.86 g of the product as a white solid. The structure was confirmed by NMR and mass spectroscopy.

Calcd. for C$_{32}$H$_{54}$N$_4$O$_6$·0.3CHCl$_3$ (MW 626.62): C, 61.91; H, 8.73; N, 8.94. Found: C, 61.86; H, 9.15; N, 9.01

EXAMPLES 22 and 23

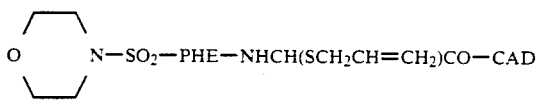

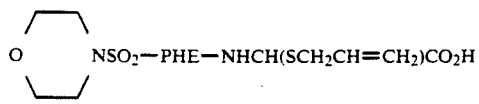

(2.0 g, 4.51 mmole) and HOBT·H$_2$O (0.67 g, 4.96 mmole) were dissolved in a mixture of 5 ml DMF and 80 ml CH$_2$Cl$_2$. After cooling to 0°, DCC (1.02 g, 4.96 mmole) and a solution of

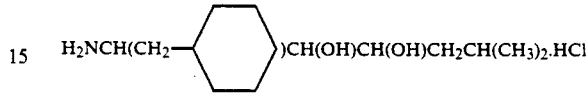

(1.36 g, 4.86 mmole) and Et$_3$N (0.7 ml, 4.96 mmole) in 25 ml cold CH$_2$Cl$_2$ were added. After stirring overnight at room temperature the mixture was filtered, evaporated under reduced pressure to a gum and redissolved in EtOAc. The solution was washed with 1N citric acid, saturated NaCl, saturated MaHCO$_3$ and saturated NaCl. The organic phase was dried over MgSO$_4$ and evaporated to a foam, 3.18 g. Chromatography on silica gel, eluting with CHCl$_3$/EtOAc (60/40) gave the faster eluting isomer as a crystalline solid, 0.79 g. The structure was confirmed by NMR and mass spectroscopy.

Calcd. for C$_{32}$H$_{52}$N$_4$O$_7$S$_2$ (MW 668.92): C, 57.46; H, 7.83; N, 8.37. Found: C, 57.50; H, 7.92; N, 8.37.

Continued elution from the column gave the slower eluting isomer as a white foam, 0.81 g. The structure was confirmed by NMR and mass spectroscopy.

Calcd. for C$_{32}$H$_{52}$N$_4$O$_7$S$_2$ (MW 668.92): C, 57.46; H, 7.83; N, 8.37. Found: C, 57.07; H, 7.72; N, 8.04.

EXAMPLES 24 and 25

BOC-PHE-NHCH(SEt)CO-CAD

A solution of 5.48 g (14.3 mmole) of BOC-PHE-NHCH(SEt)CO$_2$H and 1.97 g (14.6 mmole) of HOBT in 100 ml CH$_2$Cl$_2$ and 10 ml DMF was cooled in ice and treated with a cold solution of 4.05 g (14.3 mmole) of

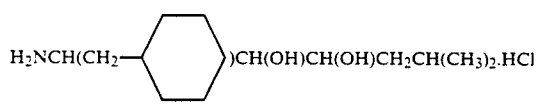

and 2.0 ml (14.6 mmole) of Et$_3$N in 70 ml CH$_2$Cl$_2$, followed by 3.0 g (14.6 mmole) of DCC. After stirring at room temperature overnight, the mixture was filtered and the solvent removed under reduced pressure. The residue was taken up in EtOAc, filtered, and extracted with 1N citric acid, saturated NaCl, saturated NaHCO$_3$, and saturated NaCl. After drying over MgSO$_4$, the solvent was removed under reduced pressure leaving 8.57 g of the crude product. Chromatography on silica gel, eluting with CHCl$_3$/EtOAc (75/25) gave the faster eluting isomer. Recrystallization from Et$_2$O/hexane gave 2.26 g of the product as a white solid. The structure was confirmed by NMR and mass spectroscopy.

Calcd. for C$_{32}$H$_{53}$N$_3$O$_6$S (MW 607.85): C, 63.23; H, 8.79; N, 6.91. Found: C, 63.34; H, 9.03; N, 6.84.

Continued elution from the column gave 2.22 g of the slower eluting isomer as a solid. The structure was confirmed by NMR and mass spectroscopy.

Calcd. for C$_{32}$H$_{53}$N$_3$O$_6$S·0.5H$_2$O (MW 616.87): C, 62.31; H, 8.82; N, 6.81. Found: C, 62.41; H, 8.79; N, 6.74.

EXAMPLE 26

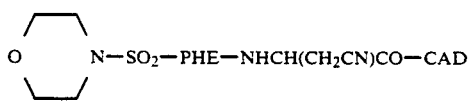

A solution of 1.57 g (5.0 mmole) of

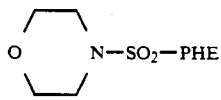

in 25 ml DMF was cooled in ice and treated with 0.67 g (5.0 mmole) HOBT and 1.03 g (5.0 mmole) of DCC. To this was then added a solution of 1.9 g (5.5 mmole) of H$_2$NCH(CH$_2$CN)CO-CAD in 15 ml DMF and the solution stirred at room temperature overnight. The mixture was filtered and the solvent removed in vacuo. The residue was taken up in EtOAc and washed with 1 N citric acid, saturated NaHCO$_3$, and saturated NaCl. Drying over MgSO$_4$ and removal of the solvent under reduced pressure gave the crude product. Chromatography on silica gel, eluting with CHCl$_3$/MeOH (95/5) gave 1.9 g of the product as a white foam, mp 203°-204.5°.

Calcd. for C$_{31}$H$_{49}$N$_5$O$_7$S·0.25CHCl$_3$ (MW 665.59): C, 56.39; H, 7.46; N, 10.52. Found: C, 56.12; H, 7.46; N, 10.34.

EXAMPLE 27

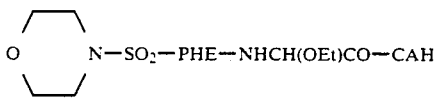

A solution of 0.77 g (1.85 mmole) of

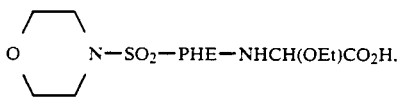

0.28 g (2.04 mmole) of HOBT, 0.5 g (1.85 mmole) of

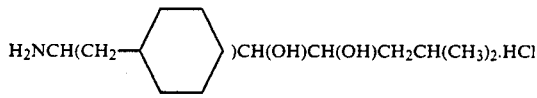

and 0.21 ml (2.04 mmole) of Et$_3$N in 25 ml DMF was cooled in ice and treated with 0.42 g (2.0 mmole) of DCC. After 0.5 hour at 0°, the mixture was allowed to stir at room temperature for 24 hours. The mixture was filtered and the residue washed with CH$_2$Cl$_2$. The combined organic phases were washed with H$_2$O, saturated NaHCO, and saturated NaCl. Drying and removal of the solvent under reduced pressure gave the crude product. Chromatography on silica gel, eluting with a gradient 0-2% MeOH in CHCl$_3$ separated the two diastereomers present. There was obtained 70 mg of the pure faster eluting diastereomer.

Calcd. for C$_{30}$H$_{50}$N$_4$O$_8$S·0.8CHCl$_3$ (MW 722.24): C, 51.22; H, 7.09; N, 7.76. Found: C, 51.27; H, 7.93; N, 7.22.

EXAMPLE 28

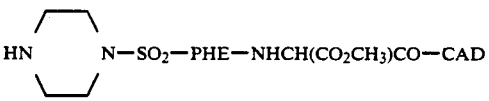

A solution of 2.3 g (2.9 mmole) of

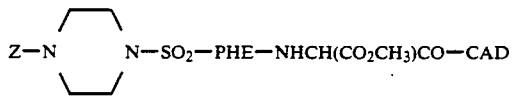

in 50 ml MeOH was treated with 0.25 g of 10% Pd/C and stirred in a hydrogen atmosphere for two hours. The mixture was filtered through Celite and the filtrate concentrated under reduced pressure to yield 1.9 g of the product. The structure was confirmed by NMR spectroscopy. The material was converted to the acetate salt and freeze-dried.

Calcd. for C$_{31}$H$_{51}$N$_5$O$_8$S·C$_2$H$_4$·1.38H$_2$O (MW 738.67): C, 53.65; H, 7.88; N, 9.48. Found: C, 53.44; H, 7.51; N, 9.41.

EXAMPLE 29

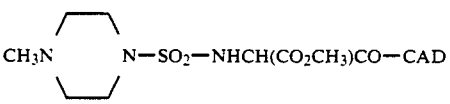

A solution of 1.1 g (1.7 mmole) of

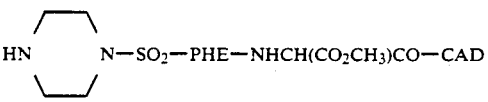

in 20 ml EtOH was treated with 0.5 ml (6.0 mmole) of 37% aqueous formaldehyde and 5 ml of formic acid and heated at reflux for three hours. The mixture was diluted with EtOAc and washed with 10% K$_2$CO$_3$ and saturated NaCl. Drying over MgSO$_4$ and removal of the solvent under reduced pressure gave the product as a foam. It was converted to the acetate salt and freeze-dried. The structure was confirmed by NMR and mass spectroscopy.

Calcd. for C$_{32}$H$_{53}$N$_5$O$_8$S·0.5C$_2$H$_4$O$_2$·1.0H$_2$O (MW 715.83): C, 55.37; H, 8.03; N, 9.78. Found: C, 55.32; H, 8.01; N, 9.73.

EXAMPLE 30

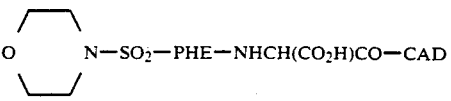

A solution of 1.2 g (1.8 mmole) of

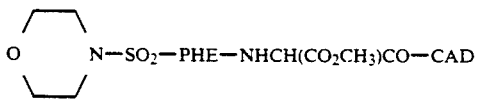

in 30 ml THF was treated with 2.7 ml of 1N MaOH and stirred at room temperature for 18 hours. The THF was removed under reduced pressure and the residue taken up in H$_2$O and washed with EtOAc. The aqueous layer was brought to pH 2.7 with 1N HCl, and the mixture extracted with EtOAc. Drying over MgSO$_4$ and removal of the solvent under reduced pressure gave 1.1 g of the product as a foam. The structure was confirmed by mass spectroscopy.

Calcd. for C$_{30}$H$_{48}$N$_4$O$_9$S·1.0H$_2$O (MW 658.73): C, 54.70; H, 7.65; N, 8.51. Found: C, 54.72; H, 7.62; N, 8.28.

EXAMPLE 31

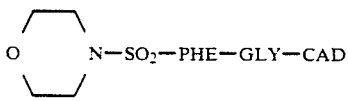

A solution of 5.55 g (16.5 mmole) of CLY-CAD·HCl in 60 ml DMF was treated with diisopropylethylamine until basic. This solution was added to a cold solution of 5.2 g (16.5 mmole) of

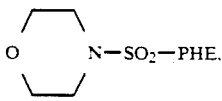

2.39 g (17.4 mmole) of HOBT, and 3.62 g (17.4 mmole) of DCC in 20 ml of DMF. After two hours at 0°, the mixture was stirred at room temperature overnight. The mixture was filtered and the filtrate concentrated under high vacuum. The residue was taken up in EtOAc and washed with 1N citric acid, saturated NaCl, saturated NaHCO$_3$, and saturated NaCl. Drying over Na$_2$SO$_4$ and removal of the solvent under reduced pressure gave 9.44 g of the crude product as a foam. Chromatography on silica gel, eluting with CHCl$_3$/MeOH (95/5) gave 7.74 g of the product as a solid foam, mp 90°–93°. The structure was confirmed by NMR and mass spectroscopy.

Calcd. for C$_{29}$H$_{48}$N$_4$O$_7$S·0.37CHCl$_3$ (MW 641.53): C, 54.99; H, 7.60; N, 8.73. Found: C, 54.94; H, 7.73; N, 8.62.

EXAMPLE 32

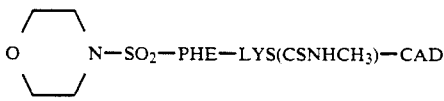

A solution of 2.1 g

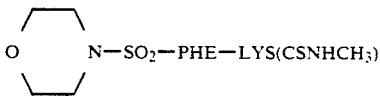

and 1.1 g HOBT in 10 ml DMF was cooled to 15° and treated with 0.8 g DCC. The mixture was stirred for 10 minutes at 15° and treated with a solution resulting from the mixing of 1.1 g

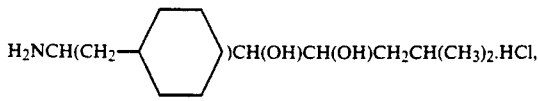

0.55 ml Et$_3$N and 10 ml CH$_2$Cl$_2$. After stirring for 48 hours at room temperature, the CH$_2$Cl$_2$ was removed under reduced pressure and the solids filtered off. The filtrate was evaporated under high vacuum and the residue taken up in CH$_2$Cl$_2$ and washed with H$_2$O, pH 7 phosphate buffer, and 5% K$_2$CO$_3$. Drying over MgSO$_4$ and removal of the solvent under reduced pressure gave the crude product. Chromatography on silica gel, eluting with CHCl$_3$/MeOH (9/1) gave the product. The appropriate fractions were combined using CH$_2$Cl$_2$ to give 1.8 g of a foam. The structure was confirmed by mass spectroscopy.

Calcd. for C$_{35}$H$_{60}$N$_6$O$_7$S$_2$·0.5CH$_2$Cl$_2$ (MW 783.35): C, 54.43; H, 7.85; N, 10.73. Found: C, 54.30; H, 7.89; N, 10.89.

EXAMPLE 33

CH$_3$O-(CH$_2$)$_2$NHSO$_2$-PHE-NHCH(CO$_2$CH$_3$)CO-CAD

Substitution of CH$_3$O-(CH$_2$)$_2$NHSO$_2$-PHE-NHCH(CO$_2$CH$_3$)CO$_2$H for

in Example 2 gives the desired product. The structure is confirmed by NMR and mass spectroscopy.

EXAMPLE 34

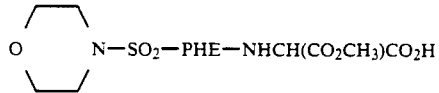

A solution of 314 mg (1.0 mmole) of

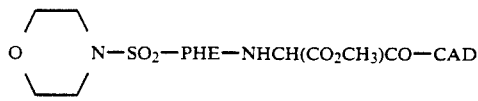

395 mg of H$_2$NCH(CO$_2$CH$_3$)CO-CAD·HCl, and 135 mg (1.0 mmole) of HOBT in 20 ml DMF is cooled in ice and 0.14 ml (1.0 mmole) of Et$_3$N added, followed by 207 mg (1.0 mmole) of DCC. After 15 minutes at 0°, the mixture is filtered and the solvent removed under high vacuum. The residue is taken up in EtOAc and washed with H$_2$O, 1N HCl, saturated NaHCO$_3$, and saturated NaCl. Drying over MgSO$_4$ and removal of the solvent under reduced pressure gives the crude product which can be purified by chromatography on silica gel. The structure is confirmed by NMR and mass spectroscopy.

INTERMEDIATES FOR EXAMPLES 1-10, 33

Me₂NSO₂-PHE

A solution of PHE (3.3 g) in 1N NaOH (20 ml) was treated with a solution of N,N-dimethylsulfamyl chloride (2.3 ml) in THF (20 ml) and stirred vigorously at 25° for three hours. The reaction mixture was then treated with additional 1NaOH (20 ml) and N,N-dimethylsulfamyl chloride (2.3 ml) and stirred three hours further at 25°. Finally 1N NaOH (20 ml) and diethyl ether (80 ml) were added. The mixture was shaken and the aqueous layer was separated and acidified to pH 1 by addition of 1N HCl (25 ml). The product was extracted into ethyl acetate, the solution dried over MgSO₄, and evaporated to give a gum which slowly solidified (4.0 g). The structure was confirmed by NMR spectroscopy.

CH₃O—(CH₂)₂NHSO₂—PHE

Prepared as above, substituting CH₃O—(CH₂)₂NHSO₂Cl (prepared according to the method of G. Weib and G. Schulze, Ann. 729, 40 (1969)) for N,N-dimethylsulfamyl chloride. The product is isolated as its dicyclohexylamine salt.

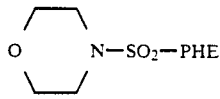

A solution of 66 g (0.4 mole) of PHE in 120 ml of 3.33N NaOH was treated dropwise over 30 minutes with a solution of 37.1 g (0.2 mole) of morpholinosulfamyl chloride (prepared according to the method of R. Wegler and K. Bodenbennen, Ann. 624, 25 (1959)) in 80 ml of THF. The solution was stirred at room temperature for six hours, then acidified to pH 2 with concentrated HCl. The mixture was extracted with EtOAc. The EtOAc phase was washed with 1N HCl, dried over MgSO₄, and evaporated to a solid. Recrystallization from H₂O gave 27 g of the pure product, m.p. 157°-158°

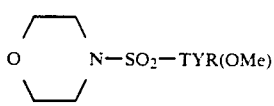

Prepared as above, substituting TYR(OMe) for PHE. The structure was confirmed by NMR spectroscopy.

Me₂NSO₂-TYR(OMe)

Prepared as above, substituting TYR(OMe) for PHE. The product was isolated as its dicyclohexylamine salt, m.p. 157°-159°.

H₂NCH(CO₂CH₃)CO₂CH₂Ph

Methyl, benzyl isonitroso malonate was prepared from methyl, benzyl malonate (obtained from Aldrich Chemical Co.) by the procedure described in *Organic Synthesis*, Col. Vol. V, p. 373. The crude product thus obtained was reduced to the title compound by the procedure described in the *Journal of the American Chemical Society*, Vol. 75, p. 1970, Apr. 20, 1953. The crude product was used without further purification in the following step.

BOC-NHCH(CO₂CH₃)CH₂CH₂Ph

H₂NCH(CO₂Me)CO₂CH₂Ph (94 g) was dissolved in ethyl ether (750 ml) and cooled to 5°. Di-t-butyldicarbonate (91.7 g) was added and the mixture was held at 4° overnight. The mixture was stripped to an orange oil (135 g). This oil was chromatographed on silica gel, eluting with hexane-ethyl acetate (85:15). The product was recovered as an oil which solidified upon standing (67 g). MS (FAB) 324 (m+1).

H₂NCH(CO₂CH₂)CO₂CH₂Ph·HCl

Treatment of BOC-NHCH(CO₂CH₃)CO₂CH₂Ph with HCl gas in CH₂Cl₂ over 5 hours afforded the desired after concentration under vacuum. The structure was confirmed by NMR and mass spectroscopy.

H₂NCH(CO₂-i-Pr)CO₂CH₂Ph·HCl

Following the procedures for preparing H₂NCH(CO₂CH₃)CO₂CH₂Ph·HCl but substituting isopropyl benzyl malonate the desired product was prepared. The structure was confirmed by NMR and mass spectroscopy.

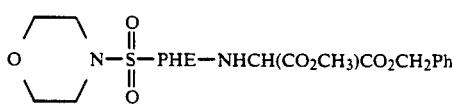

To a mixture of morpholinosulfamyl-PHE (3.14 g), H₂NCH(CO₂CH₃)CO₂CH₂Ph·HCl (2.60 g), Et₃N (1.53 ml) HOBT·H₂O (1.42 g) in DMF (50 ml) was added DCC (2.17 g) and the reaction was stirred at 25° for twenty-four hours. The reaction was filtered and concentrated under vacuum. The residue was dissolved in EtOAc (200 ml) and washed with saturated aqueous NaHCO₃ (100 ml) and three times with water (100 ml). The solution was dried over MgSO₄ and concentrated to afford the crude product which was purified by flash chromatography on silica gel.

The following compounds are obtained in an analogous manner:

CH₃O—(CH₂)₂NHSO₂—PHE—NHCH(CO₂CH₃)CO₂CH₂Ph,

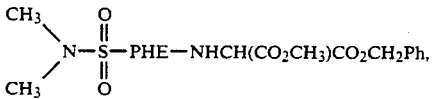

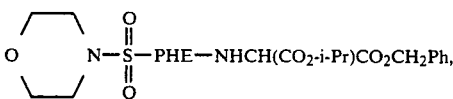

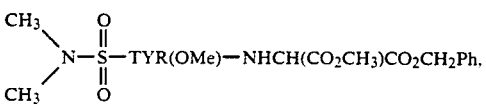

IVA—PHE—NHCH(CO₂CH₃)CO₂CH₂Ph, and

-continued

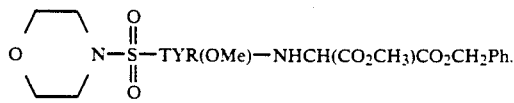

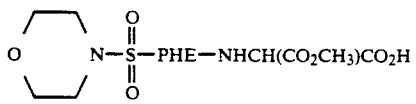

To a solution of morpholinosulfamyl-PHE-NHCH(CO2CH3)CH2CH2Ph (5.32 g) in 100 ml methanol was added 20% Pd/C (0.53 g). The suspension was stirred under a hydrogen atmosphere for three hours, filtered, and the solvent removed under reduced pressure to afford the product to sufficient purity for use in subsequent reaction.

The following compounds are prepared in an analogous manner:

CH3O—(CH2)2NHSO2—PHE—NHCH(CO2CH3)CO2H.

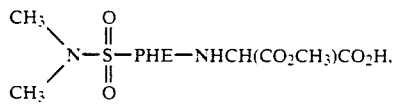

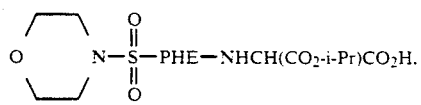

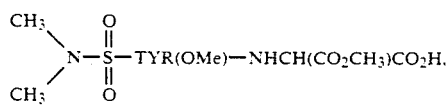

IVA—PHE—NHCH(CO2CH3)CO2H.

and

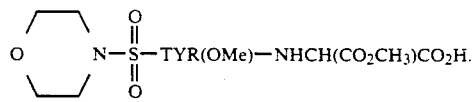

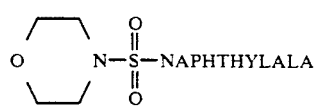

The tetra-n-butyl ammonium salt of napthylalanine (1.82 g) was dissolved in 25 ml of THF and treated with morpholinosulfamyl chloride (0.37 g). The reaction was stirred for 21 hours at 25°. The suspension was evaporated and partitioned between EtOAc (50 ml) and 1N HCl (50 ml). The EtOAc layer was separated, and washed twice with 0.5N NaOH. The combined basic layers were acidified to pH=1-2 and extracted with EtOAc (50 ml), dried over MgSO4 and concentrated. The crude product was concentrated three times from toluene (100 ml) to afford the product as a crisp foam. The structure was confirmed by NMR spectroscopy.

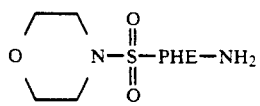

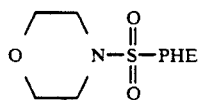

(10.0) was dissolved in a 1:1 mixture of CH2Cl2 and THF (250 ml total) and cooled to −50°. Then carbonyl diimidazole (5.4 g) was added and the reaction was warmed to −15° over a 3 hour period. Ammonia gas was bubbled into the solution for 1 hour and the reaction was allowed to warm to 20° over a 2 hour period. The reaction was concentrated to a gel and triturated with an Et2O and water mixture to afford a solid. The solid was collected, washed with water and Et2O and dried in vacuo to afford 6.0 g of product. The structure was confirmed by NMR and mass spectroscopy.

To

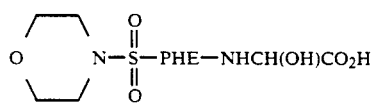

To

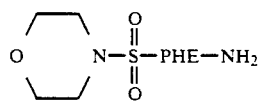

(5.9 g) in acetone (300 ml) was added glyoxylic acid·H2O (3.64 g) and the reaction was heated to reflux for two days. The reaction was then cooled and concentrated and dissolved in EtOAc. The EtOAc layer was washed with saturated sodium chloride, and twice with saturated aqueous NaHCO3. The combined basic layers were acidified to Congo Red with concentrated HCl. The aqueous layer was concentrated and taken up in EtOAc. The solids were filtered off and the EtOAc layer was washed with brine, dried over MgSO4 and concentrated to afford the product (5.27 g) as a white foam. The structure was confirmed by NMR and mass spectroscopy.

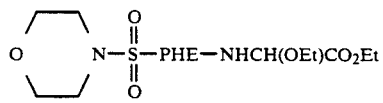

To

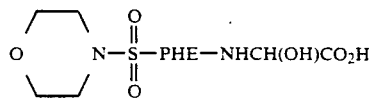

(5.11 g) dissolved in EtOH (100 ml) was added concentrated sulfuric acid (1 ml). The reaction was stirred at 25° for five days. It was then concentrated to an oil, dissolved in EtOAc and washed with saturated aqueous NaHCO3 and saturated sodium chloride. The EtOAc layer was dried over MgSO4 and concentrated. The residue was purified by flash chromatography on silica gel and the product was isolated. The structure was confirmed by NMR and mass spectroscopy.

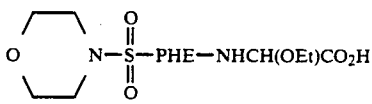

To

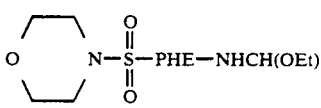

(4.11 g) dissolved in EtOH (50 ml) was added 1N HCl (23 ml) and concentrated. The residue was dissolved in EtOAc, washed with saturated sodium chloride, dried over MgSO4 and concentrated to afford the product (3.77 g) as a white foam. The structure was confirmed by NMR and mass spectroscopy.

INTERMEDIATES FOR EXAMPLES 11 AND 12

BBSP-HIS(TRT)—OCH3

A solution of 10.0 g (0.035 mole) of (+)—BBSP (EP-236,734), 14.47 g (0.035 mole) of HIS(TRT)—OCH3, and 4.75 g (0.035 mole) of HOBT in 250 ml CH2Cl2 was cooled in ice and treated with a solution of 7.25 g (0.035 mole) of DCC in 30 ml CH2Cl2, then allowed to stir at room temperature for two days. The mixture was filtered, and the filtrate washed with 1N citric acid, saturated NaHCO3, and saturated NaCl. Drying over Na2SO4 and removal of the solvent under reduced pressure gave the crude product which was purified on silica gel, eluting with a gradient of 0-2% MeOH in CHCl3. The product was crystallized from Et2O/hexane to give 12.89 g of a pale yellow solid.

BBSP—HIS(TRT)

A solution of 12.89 g (0.019 mmole) of BBSP—HIS(TRT)—OCH3 in 150 ml dioxane was cooled to 0° and 19 ml of 1N LiOH added, and the solution allowed to stir at room temperature for 16 hours. The solution was concentrated under reduced pressure acidified with NaHSO4, and extracted with CHCl3. The CHCl3 was washed with saturated NaCl and dried over Na2SO4. Removal of the solvent under reduced pressure gave 12.2 g of the product as a white solid. The structure was confirmed by NMR and mass spectroscopy.

BBSP—HIS(TRT)—CAD

A solution of 2.44 g (8.73 mmole) of

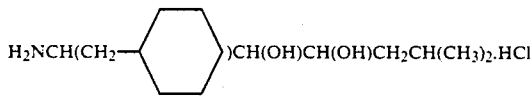

in 75 ml DMF was cooled in ice and 1.8 ml (12.9 mmole) of Et3N added. The suspension was then treated with 5.8 g (8.73 mmole) of BBSP—HIS(TRT), 1.18 g (8.73 mmole) of HOBT, and 1.8 g (8.73 mmole) of DCC. After 15 minutes at 0°, the mixture was stirred at room temperature overnight. The mixture was filtered and the DMF removed under high vacuum. The residue was taken up in EtOAc and washed with saturated NaHCO3, then with saturated NaCl. After drying over Na2SO4 and removal of the solvent under reduced pressure, the residue was chromatographed on silica gel, eluting with a gradient of 0-0.75% MeOH in CHCl3. There was obtained 1.6 g of the fast moving isomer and 2.2 g of the slow moving isomer. The structure was confirmed by NMR and mass spectroscopy.

INTERMEDIATES FOR EXAMPLES 13-15

ClCH2C≡C—CH2NHBOC

A suspension of 2.89 g (20.6 mmole) of ClCH2C≡C—CH2NH2·HCl in 30 ml of dioxane was cooled in ice and 4.5 g (20.6 mmole) of di-tert-butyldicarbonate added, followed by 10.4 ml (20.8 mmole) of 2N NaOH. The cooling was removed and the solution allowed to stir at room temperature for two hours. The solution was diluted with EtOAc and the layers separated. The EtOAc layer was washed with H2O, 1N citric acid, H2O, saturated NaHCO3, and saturated NaCl. Drying and removal of the solvent under reduced pressure left 4.2 g of the product. The material was of sufficient purity for use in the following step.

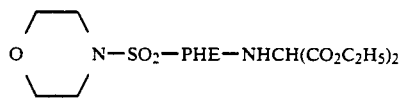

A solution of 12.57 g (0.04 mole) of

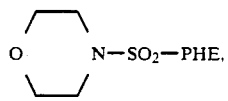

5.4 g (0.05 mole) of HOBT and 8.47 g (0.04 mole of diethyl aminomalonate·HCl in 200 ml DMF was cooled in ice and 5.6 ml (0.04 mole) of Et3N added, followed by a solution of 8.34 g (0.04 mole) of DCC in 25 ml DMF. After ½ hour at 0°, the solution was left stirring at room temperature overnight. The mixture was filtered and the solvent removed under high vacuum. The residue was taken up in EtOAc and washed with 1N HCl, H2O, saturated NaHCO3, and saturated NaCl. Drying over MgSO4 and removal of the solvent under reduced pressure left 18.1 g of the product as a viscous oil. The material was used directly in the next reaction.

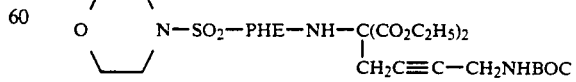

Under nitrogen, a suspension of 3.5 g (72 mmole) of NaH·mineral oil (50%) was washed free of the mineral oil with THF, then suspended in 75 ml DMSO. This suspension was treated dropwise with 17.0 g (36 mmole) of

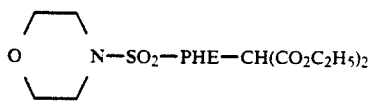

in 50 ml DMSO and stirred at room temperature. After stirring for four hours, the dark solution was treated with 7.47 g (36 mmole) of ClCH₂C≡C—CH₂NHBOC and 1.0 g of KI. After 40 hours, the solution was treated with 1N citric acid and extracted with EtOAc. The EtOAc was washed two times with H₂O, then saturated NaCl. Drying over MgSO₄ and removal of the solvent under reduced pressure left 22.7 g of a brown oil. Chromatography on silica gel, eluting with CHCl₃/MeOH (99/1) gave 14.2 g of product, sufficiently pure to use in the following reaction.

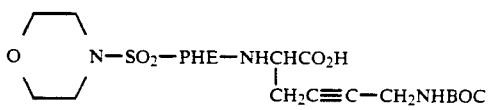

A solution of 9.82 g (15.4 mmole) of

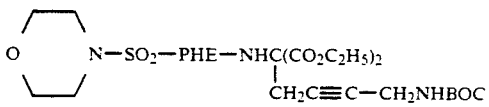

in 45 ml dioxane and 45 ml EtOH was treated with 24 ml (48 mmole) of 2N NaOH and stirred at room temperature overnight. The solvent was removed under reduced pressure and the residue taken up in H₂O and washed with Et₂O. The pH was brought to 2.5 with dilute HCl and the mixture extracted twice with EtOAc. The EtOAc was washed with saturated NaCl, dried over MgSO₄, and the solvent removed under reduced pressure. The residue was taken up in 100 ml dioxane and 100 ml toluene and heated at reflux for three hours. Removal of the solvent under reduced pressure left 7.8 g of the product as a golden brown foam. The product was sufficient pure for use in the following step.

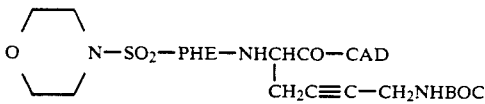

A solution of 5.65 g (1.05 mmole) of

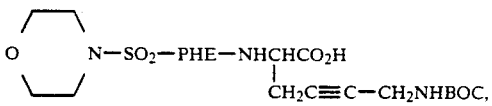

1.42 g (1.05 mmole) of HOBT and 2.93 g (1.05 mmole) of H₂NCHCH(OH)CH(OH)CH₂CH(CH₃)₂·HCl in 50 ml DMF was cooled in ice and 1.48 ml (1.05 mmole) of Et₃N added followed by 2.2 g (1.05 mmole) of DCC in 10 ml DMF. After 15 minutes at 0°, the mixture was stirred at room temperature overnight. The mixture was filtered and the solvent removed under reduced pressure. The residue was taken up in EtOAc was washed with 1N HCl, H₂O, saturated NaHCo₃, and saturated NaCl. Drying over MgSO₄ and removing the solvent under reduced pressure gave the crude product which was purified by chromatography on silica gel, eluting with CHCl₃/MeOH (99/1). There was obtained 5.36 g of pureproduct as a pale yellow foam.

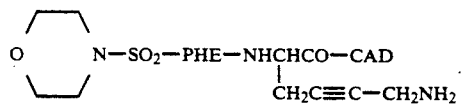

A solution of 5.3 g (6.9 mmole) of

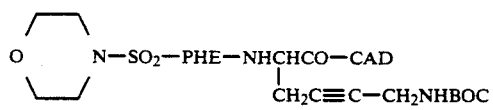

in 50 ml CH₂Cl₂ was treated with HCl gas for five minutes, then stirred at room temperature for 1.5 hours. The solvent was removed under pressure, CH₂Cl₂ added, and the solvent removed again. The residue was taken up in CH₂Cl₂ and treated with cold CH₂Cl₂ that had been saturated with ammonia. The NH₄Cl was filtered off, and the solvent removed under reduced pressure to give 4.05 g of the product as a white solid.

INTERMEDIATES FOR EXAMPLES 16 AND 17

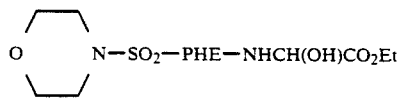

A solution of 13.0 g (33.5 mmole) of

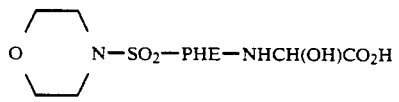

in 200 ml ab. EtOH was treated with 2 ml concentrated H₂SO₄ and stirred at room temperature overnight. Evaporation under reduced pressure gave a syrup which was taken up in EtOAc and washed with saturated NaCl, saturated NaHCO₃, 1N citric acid, and saturated NaCl. Drying over MgSO₄ and removal of the solvent under reduced pressure gave the crude product. Chromatography on silica gel, eluting with EtOAc/CHCl₃ (50/50) gave 8.75 g of the product as a white foam. The structure was confirmed by NMR and mass spectroscopy.

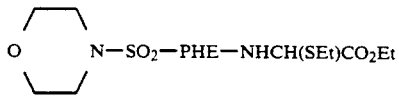

A solution of 4.4 g (10.0 mmole) of

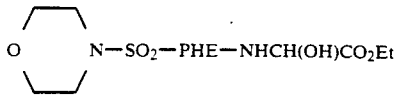

in 50 ml CH$_2$Cl$_2$ was treated with 2.6 ml (29 mmole) of EtSH and 0.15 g of anhydrous 2-naphthalenesulfonic acid and heated at reflux for two hours. The mixture was filtered and the filtrate evaporated to an oil. The oil was taken up in EtOAc and washed with saturated NaHCO$_3$, saturated NaCl, 1N citric acid, and saturated NaCl. Drying over MgSO$_4$ and removal of the solvent under reduced pressure gave the crude product as a foam. Chromatography on silica gel, eluting with CHCl$_3$/EtOAc (60/40) gave 3.83 g of the product as a glass. The structure was confirmed by NMR and mass spectroscopy.

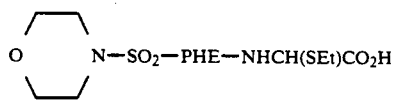

A solution of 3.54 g (7.7 mmole) of

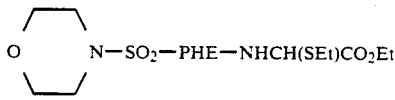

in 25 ml dioxane was treated with 15.4 ml of 1N NaOH and stirred and 45 minutes, then treated with 7.7 ml of 1N HCl. The solvent was removed under reduced pressure, an additional 7.7 ml 1N HCl added, and the material taken up in EtOAc. The EtOAc was washed with saturated NaCl, dried over MgSO$_4$, and the solvent removed under reduced pressure to give 3.37 g of the product as a foam. The structure was confirmed by NMR and mass spectroscopy. The material was used without further purification.

INTERMEDIATE FOR EXAMPLE 18

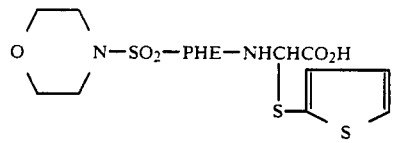

A solution of 4.07 g (10.5 mmole) of

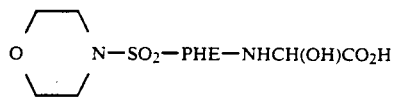

and 2.4 ml of 2-mercaptothiophene in 50 ml HOAc was cooled in ice and 5 ml concentrated H$_2$SO$_4$ added over a two minute period. After stirring at room temperature overnight, the solvent was evaporated under reduced pressure. Water was added, and the gummy precipitate taken up in Et$_2$O. The Et$_2$O phase was washed with H$_2$O, then saturated NaCl. The Et$_2$O was then extracted with saturated NaHCO$_3$, and the NaHCO$_3$ extract acidified with concentrated HCl, and then extracted with EtOAc/Et$_2$O (75/25). The organic phase was then washed with saturated NaCl and dried over MgSO$_4$. Removal of the solvent under reduced pressure gave 4.54 g of the crude product as a tan solid. Chromatography on silica gel, eluting with EtOAc/CHCl$_3$/MeOH (45/45/10) gave 2.61 ml of the product as a pale yellow foam. The structure was confirmed by NMR and mass spectroscopy.

INTERMEDIATES FOR EXAMPLES 19 AND 20

A solution of 3.0 g (7.74 mole) of

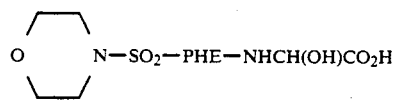

in 100 ml allyl alcohol was treated with 1 ml concentrated H$_2$SO$_4$ and stirred at room temperature overnight. The mixture was evaporated to anoil, taken up in EtOAc, and washed with saturated NaCl, saturated NaHCO$_3$, 1N citric acid, and saturated NaCl. Drying over MgSO$_4$ and removal of the solvent under reduced pressure gave 4.55 g of the crude product as an oil. Chromatography on silica gel, eluting with hexane/EtOAc (70/30) gave 2.52 g of the pure product as an oil. The structure was confirmed by NMR and mass spectroscopy.

A solution of 2.52 g (5.39 mmole) of

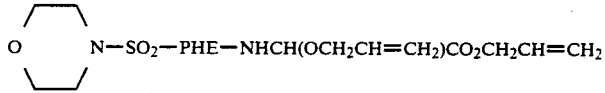

in 25 ml dioxane was treated with 10.8 ml of 1N NaOh and stirred for one hour, then treated with 5.4 ml of 1N HCl and the mixture evaporated under reduced pressure to an oil. The oil was suspended in EtOAc/Et$_2$O (75/25), 5.4 ml of 1N HCl added, and the solution washed with saturated NaCl. Drying over MgSO$_4$ and removal of the solvent under reduced pressure left 2.50 g of the product as a foam. The structure was confirmed by NMR and mass spectroscopy. The material was used without further purification.

INTERMEDIATES FOR EXAMPLE 21

Z-BMA-PHE-OMe

A solution of 6.28 g (25.0 mmole) of Z-β-aminois acid (J. Chem. Soc. 2001 (1973)) and 3.45 g (25.5 mmole) of HOBT in 150 ml $CH_2Cl_2$ was cooled in ice and a suspension of 5.39 g (25.0 mmole) of PHE-OMe·HCl and 3.55 ml (25.5 mmole) of $Et_3N$ in 100 ml of cold $CH_2Cl_2$ added, giving solution. The solution was treated with 5.26 g (25.5 mmole) of DCC and stirred at room temperature overnight. The mixture was filtered and the solvent removed under reduced pressure. The residue was taken up in EtOAc and washed with 1N citric acid, saturated NaCl, saturated $NaHCO_3$, and saturated NaCl. After drying over $MgSO_4$ the solvent was removed under reduced pressure to give 11.38 g of the crude product. Chromatography on silica gel, eluting with hexane/EtOAc (70/30) gave 9.65 g of the product as a viscous oil. The structure was confirmed by NMR and mass spectroscopy.

Z-BMA-PHE-$NH_2$

Z-BMA-PHE-OMe (4.74g, 115 mmole) was dissolved in 100 ml MeOH at $-40°$ and saturated with anhydrous $NH_3$ gas. After stirring at room temperature for two hours, the mixture was evaporated under reduced pressure to a foam, 4.49 g. The structure was confirmed by NMR and mass spectroscopy. The material was used in the following step without further purification.

Z-BMA-PHE-NHCH(OH)$CO_2H$

A solution of 4.35 9 (10.9 mmole) of Z-BMA-PHE-$NH_2$ and 1.21 g (13 mmole) of glyoxylic acid $H_2O$ in 75 ml acetone was heated at reflux for 18 hours. An additional 1.0 g of glyoxylic·$H_2O$ was added and the refluxing continued for 24 hours. An additional 0.5 g of glyoxylic acid·$H_2O$ was then added and the solution refluxed an additional 24 hours. The solvent was then removed under reduced pressure and the residue taken up in EtOAc. The EtOAc was washed with saturated NaCl, saturated $NaHCO_3$, saturated NaCl, 1N citric acid, and saturated NaCl. After drying over $MgSO_4$ and removal of the solvent under reduced pressure, there was obtained 4.86 g of the crude product. Trituration with $Et_2O$ gave 2.99 g of the product as a white foam. The structure was confirmed by mass spectroscopy. The material was used in the next step without further purification.

Z-BMA-PHE-NHCH(OEt)$CO_2Et$

A solution of 2.95 g (6.26 mmole) of Z-BMA-PHE-NHCH(OH)$CO_2H$ in 25 ml ab. EtOH was treated with 0.5 ml concentrated $H_2SO_4$ and stirred at room temperature overnight. The solvent was removed and the residue taken up in EtOAc and washed with saturated NaCl, saturated $NaHCO_3$, saturated NaCl, 1N citric acid, and saturated NaCl. After drying over $MgSO_4$, the solvent was removed under reduced pressure. The residue was twice resubjected to the reaction conditions until the reaction had gone to completion. The crude product was chromatographed on silica gel, eluting with EtOAc/$CHCl_3$ (50/50), then rechromatographed, eluting with hexane/EtOAc (75/25). There was obtained 2.46 g of the product. The structure was confirmed by NMR and mass spectroscopy.

Z-BMA-PHE-NHCH(OEt)$CO_2H$

A solution of 2.46 g (4.66 mmole) of Z-BMA-PHE-NHCH(OEt)$CO_2Et$ in 60 ml dioxane was treated with 9.3 ml of 1N NaOH and stirred at room temperature for one hour, then treated with 4.66 ml of 1N HCl and the solvent removed under reduced pressure. An additional 4.66 ml of 1N HCl was added and the residue taken up in EtOAc and washed with saturated NaCl. After drying over $MgSO_4$ the solvent was removed under reduced pressure to give 1.31 g of the product as a white foam. The structure was confirmed by mass spectroscopy.

Z-BMA-PHE-NHCH(OEt)CO-CAD

A solution of 1.31 g (2.91 mmole) of Z-BMA-PHE-NHCH(OEt)$CO_2H$ and 0.4 g (2.97 mmole) of HOBT in 50 ml $CH_2Cl_2$ and 4 ml DMF was cooled in ice and treated 0.62 g (2.97 mmole) of DCC followed by a cold solution of 0.82 g (2.91 mmole) of

and 0.42 ml (2.97 mmole) of $Et_3N$ in 20 ml $CH_2Cl_2$. After stirring overnight at room temperature, the mixture was filtered and the solvent removed under reduced pressure. The residue was taken up in EtOAc, filtered, and washed with 1N citric acid, saturated NaCl, saturated $NaHCO_3$, and saturated NaCl. Drying over $MgSO_4$ and removal of the solvent under reduced pressure gave the crude product. Chromatography on silica gel, eluting with $CHCl_3$/EtOAc (75/25) give 1.58 g of the product as a white foam.

INTERMEDIATE FOR EXAMPLES 22 AND 23

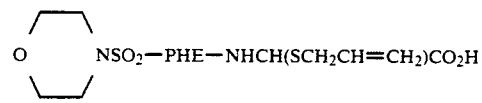

A solution of 17.4 g (44.9 mmole) of

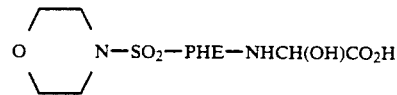

in 250 ml HOAc was cooled in ice and 20.6 ml (181 mmole) of 70% allyl mercaptan added, followed by 15 ml of concentrated $H_2SO_4$. The mixture was stirred at room temperature overnight and the solvent then removed under reduced pressure. The residue was mixed with ice and extracted with $Et_2O$. The $Et_2O$ was washed with saturated NaCl, then saturated $NaHCO_3$. The $NaHCO_3$ wash was brought to pH 1 with concentrated HCl and extracted with $Et_2O$. The $Et_2O$ was washed with saturated NaCl. Drying over $MgSO_4$ and removal of the $Et_2O$ under reduced pressure left the crude product. Chromatography on silica gel, eluting with $CHCl_3$/MeOH (96/4) gave the product. Crystallization from EtOAc/isopropyl ether gave 4.0 g of a solid. The structure was confirmed by NMR and mass spectroscopy.

INTERMEDIATES FOR EXAMPLES 24 AND 25

BOC-GLY-OCH₂CCl₃

A solution of 26.28 g (0.15 mole) of BOC-GLY and 27 g (0.18 mole) of 2,2,2-trichloroethanol in 250 ml CH₂Cl₂ was cooled in ice and 0.18 g of 4-dimethylaminopyridine added, followed by 31.6 g (0.153 mole) of DCC. After stirring at room temperature for 3.5 hour, the mixture was filtered and the solvent removed under reduced pressure. The residue was taken up in EtOAc and washed with 1N citric acid, saturated NaCl, saturated NaHCO₂, and saturated NaCl. Drying over MgSO₄ and removal of the solvent under reduced pressure left the crude product. Chromatography on silica gel, eluting with hexane/EtOAo (90/10) gave 45.0 g of the product as a crystalline solid. The structure was confirmed by NMR and mass spectroscopy.

BOC-NHCH(Br)CO₂CH₂CCl₃

BOC-GLY-OCH₂CCl₃ (22.5 g, 73.3 mmole) and N-bromosuccinimide (22.5 g, 73.4 mmole) was added to 300 ml CCl₄ in a quartz reaction flask illuminated by a Corex-filtered 450 watt Hanovia mercury lamp and irradiated for one hour at 40°. The succinimide was filtered off and the filtrate was evaporated to a white, crystalline solid 26.85 g. The structure was confirmed by NMR. The material was used without further purification in the following reaction.

BOC-NHCH(SEt)CO₂CH₂CCl₃

A suspension of 1.2 g (25 mmole) of NaH·mineral oil (50%) was washed free of mineral oil with THF, then resuspended in 100 ml of THF, and treated with 2.15 ml (29 mmole) of ethanethiol. After one hour at room temperature, the suspension was cooled to 0° and a solution of 9.46 g (25 mmole) of BOC-NHCH(Br)CO₂CH₂CCl₃ in 50 ml THF was added over 15 minutes, and the mixture left stirring at room temperature overnight. The solvent was removed under reduced pressure and the residue taken up in EtOAc and washed with 1N citric acid, saturated NaCl, saturated NaHCO₃, and saturated NaCl. Drying over MgSO₄ and removal of the solvent under reduced pressure left 7.11 g of the crude product as a red oil. Chromatography on silica gel, eluting with hexane/EtOAc (70/30) gave 7.56 g of the product as a yellow oil. The structure was confirmed by NMR and mass spectroscopy. Some replacement of the trichloroethyl group by ethanethiol had occurred. The crude material was used in the following reaction.

H₂NCH(SEt)CO₂CH₂CCl₂·HCl

BOC-NHCH(SEt)CO₂CH₂CCl₃ (7.04 g, 19.2 mmole) was dissolved in 200 ml CH₂Cl₂ and occasionally purged with anhydrous HCl gas over five hours. After standing at room temperature overnight, the mixture was filtered and evaporated under reduced pressure to an orange oil. Trituration with Et₂O gave an orange syrup, 5.47 g. The structure was confirmed by NMR, which also showed the presence of some H₂NCH(SEt)-COSEt·HCl. The crude material was used in the following reaction without further purification.

BOC-PHE-NHCH(SEt)CO₂CH₂CC₃

A solution of 4.71 g (17.7 mmole) of BOC-PHE, 2.47 g (18.3 mmole) of HOBT, and 5.38 g (17.7 mmole) of H₂NCH(SEt)CO₂CH₂CCl₃·HCl in 125 ml CH₂Cl₂ was cooled in ice and 3.78 g (18.3 mmole) of DCC was added, followed by 4.1 ml (28.9 mmole) of Et₃N. After stirring at room temperature overnight, the mixture was filtered and the solvent removed under reduced pressure. The residue was taken up in EtOAc, filtered, and washed with 1N citric acid, saturated NaCl, saturated NaHCO₃, and saturated NaCl. Drying over MgSO₄, treating with charcoal, and removal of the solvent under reduced pressure gave 9.43 g of the crude product as a dark red oil. Chromatography on silica gel, eluting with hexane/EtOAc (80/20) gave 6.08 g of the product as a white foam. The structure was confirmed by NMR and mass spectroscopy, which also showed the presence of some BOC-PHE-NHCH(SEt)COSEt. The material was used in the next reaction without further purification.

BOC-PHE-NHCH(SEt)CO₂H

A solution of 5.89 g (11.5 mmole) of BOC-PHE-NHCH(SEt)CO₂CH₂CCl₃ in 25 ml dioxane was treated with 20 ml of 1N NaOH and stirred for two hours. The solution was then treated with 12 ml of 1N HCl and the solvent evaporated. The residue was taken up in EtOAc and 12 ml of 1N HCl. The organic phase was washed with saturated NaCl and dried over MgSO₄. Removal of the solvent under reduced pressure gave 5.96 g of the product as a foam. The structure was confirmed by NMR and mass spectroscopy.

INTERMEDIATES FOR EXAMPLE 26

Z-NHCH(CH₂CN)CO₂H

A solution of 33.6 g (0.126 mole of Z-ASN in 250 ml pyridine was treated with 27.5 g (0.133 mole) of DCC and stirred at room temperature overnight. The mixture was filtered and the filtrate evaporated. The residue was taken up in H₂O, filtered, and the pH brought to 2 with dilute HCl. After cooling overnight, the product was collected and recrystallized from 1,2-dichloroethane to give 20.6 g of product.

Z-NHCH(CH₂CN)CO-CAD

A solution of 1.78 g (7.2 mmole) of Z-NHCH(CH₂CN)CO₂H and 0.97 g (7.3 mmole) of HOBT in 50 ml of CH₂Cl₂ was cooled in ice and treated with 1.48 g (7.3 mmole) of DCC, followed by a solution of 2.0 g (7.2 mmole) of

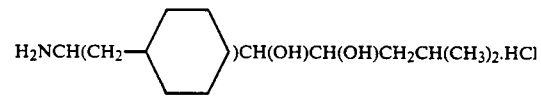

and 0.93 g (7.5 mmole) of diisopropylethylamine in 20 ml CH₂Cl₂. After two hours at 0°, the solution was stirred at room temperature overnight. The mixture was filtered and the filtrate washed with 1N citric acid, saturated NaHCO₃, and saturated NaCl. Drying over MgSO₄ and removal of the solvent under reduced pressure left a white solid. Recrystallization from EtOAc provided 2.6 g of the pure product.

H₂NCH(CH₂CN)CO-CAD

A solution of 2.6 g (5.5 mmole) of Z-NHCH(CH₂CN)CO-CAD in 30 ml MeOH was treated with 0.4 g of 5% Pd/C and stirred in a hydrogen atmosphere for 2.5 hours. The mixture was filtered and the filtrate evaporated in vacuo to give 1.9 g of the product as a foam.

INTERMEDIATES FOR EXAMPLE 27

BOC-CYCLOHEXYLGLYCINE

A solution of 94.4 g (2.66 mole) of BOC-phenylglycine in 1 l of 2-propanol was treated with 5 g of 10% Rh/C and reduced at 25°, 50 psi. The mixture was filtered and the solvent removed under reduced pressure The product was used without further purification.

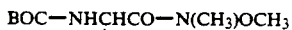
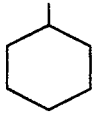

A solution of 102 g (0.4 mole) of BOC-cyclohexylglycine in 600 ml CH₂Cl₂ was cooled to −50° and 58.4 ml (0.48 mole) of N-methylpiperidine added followed by 42 ml (0.44 mole) of ethyl chloroformate. This solution was added dropwise to a solution of 42.5 g (0.44 mole) of O,N-dimethylhydroxylamine·HCl and 58.4 ml (0.4 mole) of N-methylpiperidine in 200 ml CH₂Cl₂. After 30 minutes the mixture was washed with 10% citric acid, saturated NaHCO₃, and saturated NaCl. After drying, the solution was filtered through silica gel, and the solvent removed under reduced pressure. There was obtained 87.6 g of the product. The structure was confirmed by NMR spectroscopy.

BOC-CYCLOHEXYLGLYCINAL

A solution of 40 g (0.119 mole) of BOC-CYCLOHEXYLGLYCINE, O,N-DIMETHYLHYDROXAMIDE in 550 ml Et₂O was cooled in ice and 148 ml (0.148 mole) of a 1M solution of LiAlH₄ in Et₂O added over 0.5 hour. After an additional 15 minutes, the mixture was treated cautiously with 28 g of KHSO₄ in 100 ml H₂O. The mixture was filtered through Celite and washed with 10% citric acid and saturated NaHCO₃. After drying the solvent was removed under reduced pressure to give the crude BOC-CYCLOHEXYLGLYCINAL. The material was used immediately in the following reaction.

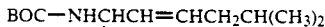
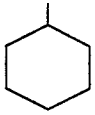

To a suspension of 23.8 g (0.19 mole) of KH (as a 35% suspension in mineral oil) in 100 ml DMSO at −5° was added dropwise over one hour, 42.1 ml (0.199 mole) of hexamethyldisilazane. This was then treated with 78.35 g (0.19 mole) of the triphenylphosphonium salt derived from isovaleryl bromide. After cooling to −78°, the mixture was treated with 23 g (0.095 mole) of BOC-CYCLOHEXYLGYCINAL in 100 ml of toluene. After stirring at room temperature overnight, the mixture was washed with H₂O, saturated NaCl, and saturated NaHCO₃. Drying and removal of the solvent under reduced pressure gave the crude product. Chromatography on silica gel, eluting with CHCl₃/hexane (80/20) gave 19 g of the product. The structure was confirmed by NMR spectroscopy.

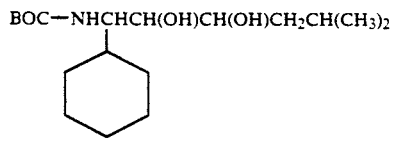

A solution of 5.25 g (18.0 mmole) of

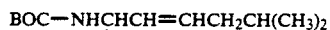
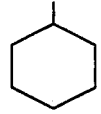

in 100 ml THF was treated with 6.0 g (44 mmole) of 4-methylmorpholine, N-oxide and 0.05 g (0.18 mmole) of osmium tetroxide and the mixture stirred at room temperature for four days. The THF was then removed under reduced pressure and the residue taken up in EtOAc and washed with 10% Na₂SO₃, 10% citric acid, saturated NaHCO₃, and saturated NaCl. Drying and removal of the solvent under reduced pressure gave the crude product. The desired diastereomer could be isolated by chromatography on silica gel, eluting a gradient of 10-30% EtOAc in hexane. There was obtained 1.87 g of product.

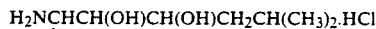
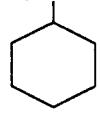

A solution of 1.87 g (5.71 mmole) of

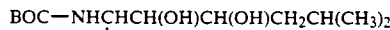
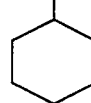

in 50 ml of 2N HCl in MeOH was allowed to stand overnight. Removal of the solvent under reduced pressure left 1.5 g of the product. The structure was confirmed by NMR spectroscopy.

INTERMEDIATES FOR EXAMPLE 28

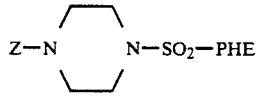

L-Phenylalanine (1.65 g) was converted to its tetramethyl ammonium salt and dissolved in a mixture of THF (50 ml) and 2-propanol (12 ml). 4-Carbobenzyloxypiperazinosulfamyl chloride (1.59 g) was added and the reaction was stirred for 16 hours in a stoppered flask. The resulting suspension was evaporated and the residue was partitioned between dichloromethane and 1N HCl. The organic layer was washed with 1N HCl then extracted with 0.3N NaOH. The basic extract was immediately acidified to pH 1 with concentrated HCl and extracted with ethyl acetate. This extract was dried over magnesium sulfate and evaporated to give the desired product as an off-white solid 1.35 g). The structure was confirmed by NMR spectorscopy.

BOC-AMINOMALONIC ACID, METHYLESTER

To a solution of 16.17 g (13.5 mmole) of BOX-aminomalonic acid, methyl benzyl ester in 250 ml MeOH was added 0.66 g of 20% Pd/C catalyst. The suspension was purged with hydrogen gas for 1.5 hours, after which the suspension was filtered and the solvent removed under reduced pressure at 30°, giving a syrup, 12.5 g. The product was kept at 4° until used in the following reaction.

BOC-NHCH(CO₂CH₃)CO-CAD

A solution of 2.2 g (9.4 mmole) of BOC-aminomalonic acid, methyl ester, 1.34 g (9.9 mmole) of HOBT, 2.89 g (10 mmole) of

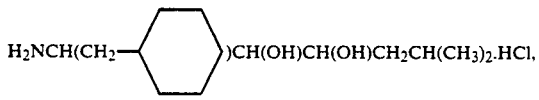

and 1.5 ml (10 mmole) of Et₃N in 100 ml CH₂Cl₂ was cooled in ice and treated with 2.04 g (9.9 mmole) of DCC in 100 ml of CH₂Cl₂. After 0.5 hour at 0°, the mixture was allowed to stir at room temperature for 24 hours. The mixture was filtered and washed with H₂O, saturated NaHCO₃, and saturated NaCl. Drying and removal of the solvent under reduced pressure gave the crude product. Chromatography on silica gel, eluting with CH₂Cl₂/MeOH (9/1) gave 2.2 g of product. The structure was confirmed by NMR and mass spectroscopy.

H₂NCH(CO₂CH₃)CO-CAD·HCl

A solution of 6.25 g (14 mmole) of BOX-NHCH(CO₂CH₃)CO-CAD in 65 ml of 2.3M HCl in MeOH was stirred at room temperature overnight. The solvent was removed under reduced pressure giving the product. The structure was confirmed by NMR and mass spectroscopy. The product was used in the next reaction without further purification.

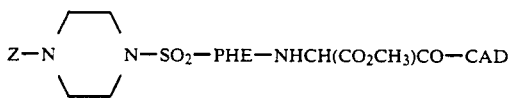

A solution of 2.36 g (5.3 mmole) of

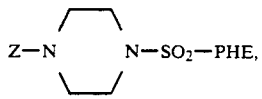

0.72 g (5.3 mmole) of HOBT, 1.99 g (5.0 mmole) of

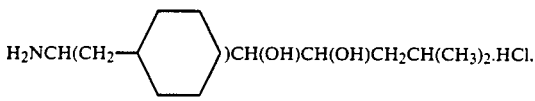

and 0.74 ml (5.3 mmole) of Et₃N in 60 ml CH₂Cl₂ was cooled in ice and treated with 1.09 g (5.3 mmole) of DCC in 10 ml CH₂Cl₂. After 0.5 hour at 0°, the mixture was allowed to stir at room temperature for 48 hours. The mixture was filtered, and the filtrate washed with H₂O, saturated NaHCO₃, and saturated NaCl. Drying and removal of the solvent under reduced pressure gave the crude product. Chromatography on silica gel, eluting with CH₃Cl₂/MeOH (9/1) gave 2.5 g of the product. The structure was confirmed by NMR and mass spectroscopy.

INTERMEDIATES FOR EXAMPLE 31

BOC-GLY-CAD

A solution of 2.66 g (15.2 mmole) of BOC-GLY, 2.2 g (15.9 mmole) of HOBT, 4.25 g (15.2 mmole of

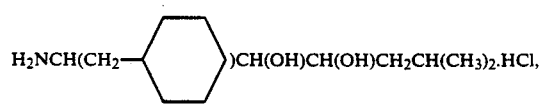

and 2.16 ml (15.5 mmole) of Et₃N in 40 ml DMF was cooled in ice and treated with 3.32 g (15.9 mmole) of DCC in 5 ml DMF. After two hours at 0°, the mixture was allowed to stir at room temperature for 24 hours. The mixture was filtered and the filtrate concentrated under high vacuum. The residue was taken up in EtOAc and washed with H₂O, 1N citric acid, saturated NaHCO₃, and saturated NaCl. Drying and removal of the solvent under reduced pressure gave the crude product. Chromatography on silica gel, eluting with CHCl₃/MeOH (97.5/2.5) gave 6.6 g of the product. The structure was confirmed by NMR and mass spectroscopy.

GLY-CAD·HCl

A solution of 6.62 g (16.5 mmole) of BOX-GLY-CAD in 60 ml CH₂Cl₂ was treated with 30 ml of TFA and stirred at room temperature for two hours. The solvent was removed under reduced pressure, CH₂Cl₂ added, and the solvent removed again. The residue was then taken up in CH₂Cl₂ and HCl gas bubbled in. Removal of the solvent under reduced pressure gave the product. The material was used in the next reaction without further purification.

INTERMEDIATES FOR EXAMPLE 32

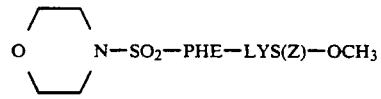

A mixture of N-(4-morpholinosulfonyl)-PHE (3.15 g, 10 mmole), DCC (2.1 g, 10 mmole), HOBT (1.3 g, 10 mmole) and DMF (20 ml) was stirred at 20° for five minutes. The resulting slurry was treated consecutively with LYS(Z)—OCH₃·HCl (3.32 g, 10 mmole), Et₃N (1.4 ml, 10 mmole) and CH₂Cl₂ (10 ml). The reaction was stirred for 48 hours at 20° then CH₂Cl₂ was evaporated. Ethyl acetate was added and the solids were removed by filtration. Evaporation of the filtrate gave a wet solid that was triturated with water, dissolved in CHCl₃ and washed with 5% K₂CO₃. The organic layer was dried over MgSO₄ and evaporated to a pale yellow solid. Trituration with ethyl acetate gave 5.3 g of a colorless solid.

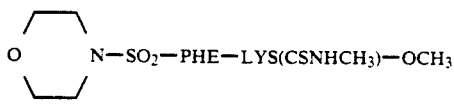

A solution of

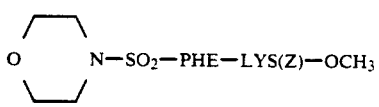

(5.28 g, 8.95 mmole) in THF (125 ml) was treated with 20% Pd/C (0.55 g) and stirred under an atmosphere of hydrogen. After three hours, methanol (125 ml) was added and catalyst removed by filtration. The resulting solution was treated with methyl isothiocyanate (0.7 g, 9.6 mmole) and stirred 18 hours at 20°. Evaporation gave a solid that was recrystallized from hot CHCl₃ by dropwise addition of ether to give the desired product (4.25 g). The structure was confirmed by mass spectroscopy.

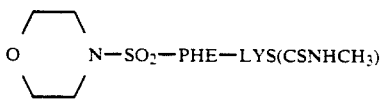

A solution of 4.25 g (8.2 mmole) of

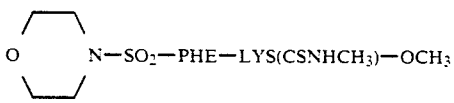

in 50 ml THF was treated with 20 ml of 1N NaOH and stirred at room temperature for 24 hours. The solution was diluted with H₂O and the pH brought to two with 2N HCl. The solution was extracted with CH₂Cl₂. Drying the organic layer over MgSO₄ and removal of the solvent under reduced pressure left 3.98 g of the product. The structure was confirmed by mass spectroscopy.

INTERMEDIATES FOR EXAMPLE 34

BOC—NHCH(CO₂CH₃)CO—NHCHCH=CH—CH₂CH(CH₃)₂
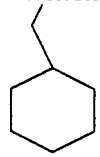

A solution of 234 mg (1.0 mmole) of BOC-NHCH(CH₂CH₃CO₂H, 210 mg (1.0 mmole) of

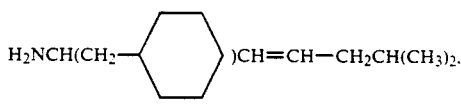

and 135 mg (1.0 mmole of HOBT in 15 ml DMF is cooled in ice and 207 mg (1.0 mmole) of DCC added. After 0.5 hour at 0°, the mixture is allowed to stir at room temperature overnight. The mixture is filtered and the solvent removed under high vacuum. The residue is taken up in EtOAc and washed with H₂O, 1N HCl, saturated NaHCO₃, and saturated NaCl. Drying over MgSO₄ and removal of the solvent under reduced pressure gives the crude product which can be purified by chromatography on silica gel. The structure is confirmed by NMR and mass spectroscopy.

BOC-NHCH(CO₂CH₃)CO-CAD

A solution of 4.24 g (10 mmole) of

BOC—NHCH(CO₂CH₃)CO—
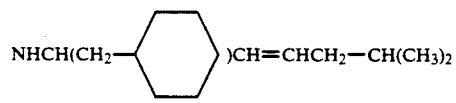

in 100 ml THF is treated with 3.5 g (30 mmole) of N-methylmorpholine-N-oxide and 100 mg (0.4 mmole) of osmium tetroxide is added. After stirring for 72 hours, the mixture is filtered and concentrated under reduced pressure. The residue is taken up in EtOAc and washed with 10% Na₂SO₄, 10% citric acid, saturated NaHCO₃, and saturated NaCl. Removal of the solvent under reduced pressure gives the crude product. The correct product is isolated by chromatography on silica gel.

H₂NCH(CO₂CH₃)CO-CAD·HCl

A solution of 4.58 g (10 mmole) of BOC-NHCH(CO₂CH₃CO-CAD in 50 ml CH₂Cl₂ is saturated with HCl gas and left stirring for two hours. The solvent is removed under reduced pressure, CH₂Cl₂ is added and the solvent removed again. The crude product is thus obtained, sufficiently pure for use in the next reaction.

We claim:

1. A peptide of the formula $$A-X-Y-W- \qquad I$$

or a pharmaceutically acceptable acid addition salt thereof, wherein

A is

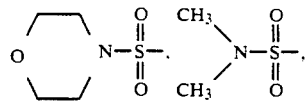

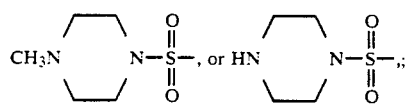

X is PHE, NAPHTHYLALA, or TYR(OMe);

W is

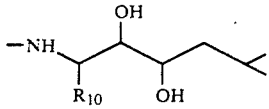

wherein $R_{10}$ is cyclohexyl or cyclohexylmethyl;
Y is

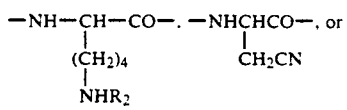

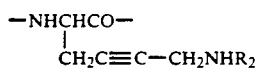

wherein $R_2$ is

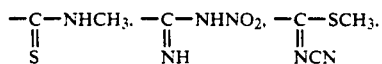

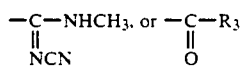

wherein $R_3$ is hydrogen, lower alkyl, or aryl.

2. A peptide named:

BBSP-HIS-CAD.

3. A pharmaceutical composition comprising a renin-inhibitory effective amount of a peptide as claimed in claim 1 together with a pharmaceutically acceptable carrier.

4. A method of treating renin-associated hypertension which comprises administering to a mammal a pharamaceutical composition as claimed in claim 1.

5. A method of treating hyperaldosteronism which comprises administering to a mammal a pharmaceutical composition as claimed in claim 1.

6. A method of treating congestive heart failure which comprises administering to a mammal a pharmaceutical composition as claimed in claim 1.

7. A compound select from

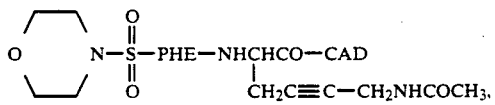

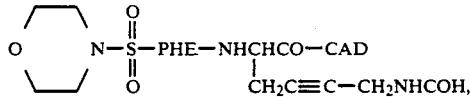

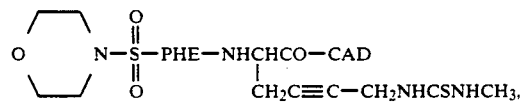

and

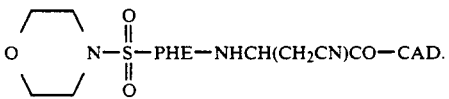

* * * * *